(12) United States Patent
Rademacher et al.

(10) Patent No.: US 10,300,022 B2
(45) Date of Patent: May 28, 2019

(54) NANOPARTICLE DELIVERY COMPOSITIONS

(71) Applicant: Midatech Limited, Abingdon (GB)

(72) Inventors: Thomas Rademacher, Oxfordshire (GB); David K. Male, Milton Keynes (GB)

(73) Assignee: Midatech Ltd., Oxfordshire (GB)

( * ) Notice: Subject to any disclaimer, the term of this patent is extended or adjusted under 35 U.S.C. 154(b) by 380 days.

(21) Appl. No.: 14/175,422

(22) Filed: Feb. 7, 2014

(65) Prior Publication Data

US 2014/0227186 A1    Aug. 14, 2014

(30) Foreign Application Priority Data

Feb. 12, 2013   (GB) .................................. 1302427.8

(51) Int. Cl.
| | | |
|---|---|---|
| *A61K 9/51* | (2006.01) | |
| *A61K 9/00* | (2006.01) | |
| *A61K 49/18* | (2006.01) | |
| *B82Y 5/00* | (2011.01) | |
| *A61K 38/17* | (2006.01) | |
| *A61K 39/395* | (2006.01) | |

(52) U.S. Cl.
CPC .......... *A61K 9/5123* (2013.01); *A61K 9/0009* (2013.01); *A61K 9/5115* (2013.01); *A61K 9/5192* (2013.01); *A61K 38/1709* (2013.01); *A61K 39/3955* (2013.01); *A61K 49/1824* (2013.01); *B82Y 5/00* (2013.01); *Y10S 977/773* (2013.01); *Y10S 977/788* (2013.01); *Y10S 977/81* (2013.01); *Y10S 977/906* (2013.01); *Y10S 977/93* (2013.01)

(58) Field of Classification Search
CPC .............. A61K 9/5123; A61K 39/3955; A61K 38/1709; A61K 9/0009; A61K 9/5115; A61K 9/5192; A61K 49/1824; B82Y 5/00; Y10S 977/906; Y10S 977/93; Y10S 977/773; Y10S 977/788; Y10S 977/81
See application file for complete search history.

(56) References Cited

U.S. PATENT DOCUMENTS

| | | | |
|---|---|---|---|
| 2007/0141133 A1 | 6/2007 | Wang et al. | |
| 2008/0226917 A1* | 9/2008 | Zhong ...................... | B01J 13/02 428/403 |
| 2010/0034735 A1* | 2/2010 | Chen ..................... | A61K 9/5115 424/1.29 |
| 2010/0260686 A1* | 10/2010 | Zhang .................. | A61K 47/489 424/9.322 |
| 2012/0009260 A1* | 1/2012 | Schobel ............... | A61K 9/0056 424/484 |
| 2012/0301535 A1 | 11/2012 | Williams et al. | |
| 2013/0344125 A1* | 12/2013 | Govender ............ | A61K 9/0024 424/423 |

FOREIGN PATENT DOCUMENTS

| | | |
|---|---|---|
| EP | 2305310 A1 | 4/2011 |
| JP | 2008533203 A | 8/2008 |
| WO | 02/32404 A2 | 4/2002 |
| WO | 2004/108165 A2 | 12/2004 |
| WO | 2005/091704 A2 | 10/2005 |
| WO | 2005/116226 A2 | 12/2005 |
| WO | 2006/037979 A2 | 4/2006 |
| WO | 2006/102377 A2 | 9/2006 |
| WO | 2007/015105 A2 | 2/2007 |
| WO | 2007/122388 A2 | 11/2007 |
| WO | 2011/154711 A1 | 12/2011 |

OTHER PUBLICATIONS

Sharma et al., Langmuir 2012, 28, 15958-15965.*
Alkilany, Alaaldin M. et al., "Toxicity and cellular uptake of gold nanoparticles: what we have learned so far?", J. Nanopart. Res., 12: 2313-2333 (2010).
Baker, David et al., "Gene therapy in autoimmune, demyelinating disease of the central nervous system", Gene Therapy, 10: 844-853 (2003).
Chen, Lei et al., "Manufactured Aluminum Oxide Nanoparticles Decreae Expression of Tight Junction Proteins in Brain Vasculature", J. Neuroimmune Pharmacol., 3: 286-295 (2008).
Chen, Yu-Shiun et al., "Assessment of the In Vivo Toxicity of Gold Nanoparticles", Nanoscale Res. Lett, 4: 858-864 (2009).
Deverman, Benjamin E. et al., "Exogenous Leukemia Inhibitory Factor Stimulates Oligodendrocyte Progenitor Cell Proliferation and Enhances Hippocampal Remyelination", The Journal of Neuroscience, 32(6): 2100-2109 (2012).
Etame, Arnold B. et al., "Design and potential application of PEGylated gold nanoparticles with size-dependent permeation through brain microvasculature", Nanomedicine: Nanotechnology, Biology, and Medicine, 7: 992-1000 (2011).
Gao, Huajian et al., "Mechanics of receptor-mediated endocytosis", PNAS, 102(27): 9469-9474 (2005).
Kanwar, Jagat et al., "Nanoparticles in the treatment and diagnosis of neurological disorders: untamed dragon with fire power to heal", Nanomedicine: Nanotechnology, Biology, and Medicine, 8: 399-414 (2012).
Manfredsson, Fredric P. et al., "Development of Gene Therapy for Neurological Disorders", Discovery Medicine, 9(46): 204-211 (2010).
Patel, Toral et al., "Polymeric nanoparticles for drug delivery to the central nervous system", Advanced Drug Delivery Reviews, 64: 701-705 (2012).

(Continued)

*Primary Examiner* — Robert S Cabral
(74) *Attorney, Agent, or Firm* — Kathleen D. Rigaut; Howson & Howson LLP

(57) ABSTRACT

Nanoparticle delivery systems for use in targeting biologically active agents to the central nervous system comprise a composition comprising (a) a nanoparticle comprising: (i) a core comprising a metal and/or a semiconductor; and (ii) a corona comprising a plurality of ligands covalently linked to the core, wherein said ligands comprise a carbohydrate, insulin and/or a glutathione; and (b) the at least one agent to be delivered to the CNS. Methods of treatment and diagnosing CNS disorders utilizing the nanoparticle delivery systems and related screening methods are also disclosed.

3 Claims, 28 Drawing Sheets

(56) References Cited

OTHER PUBLICATIONS

Sarkadi, Balazs et al., "Human Multidrug Resistance ABCB and ABCG Transporters: Participation in a Chemoimmunity Defense System", Physiol. Rev., 86: 1179-1236 (2006).
Shan, Yuping et al., "Size-dependent endocytosis of single gold nanoparticles", Chem. Commun., 47: 8091-8093 (2011).
Sloane, Evan et al., "Anti-inflammatory cytokine gene therapy decreases sensory and motor dysfunction in experimental Multiple Sclereosis: MOG-EAE behavorial and anatomical symptom treatment with cytokine gene therapy", Brain, Behavior, and Immunity, 23: 92-100 (2009).
Sonavane, Ganeshchandra et al., "Biodistribution of colloidal gold nanoparticles after intravenous administration: Effect of particle size", Colloids and Surfaces B: Biointerfaces, 66: 274-280 (2008).
Wolburg, Hartwig et al., "Tight junctions of the blood-brain barrier: Development, composition and regulation", Vascular Pharmacology, 38: 323-337 (2002).
Zensi, Anja et al., "Human serum albumin nanoparticles modified with apolipoprotein A-I cross the blood-brain barrier and enter the rodent brain", Journal of Drug Targeting, 18(10): 842-848 (2010).
Zhang, Sulin et al., "Size-Dependent Endocytosis of Nanoparticles", Adv. Mater., 21: 419-424 (2009).
Chithrani, B. Devika et al., "Determining the Size and Shape Dependence of Gold Nanoparticle Uptake into Mammalian Cells", Nano Letters, 6(4): 662-668 (2006).
Cho, Eun Chul et al., "The effect of sedimentation and diffusion on cellular uptake of gold nanoparticles", Nature Nanotechnology, 6: 385-391 (2011).
De la Fuente, Jesus M. et al., "Tat Peptide as an Efficient Molecule to Translocate Gold Nanoparticles into the Cell Nucleus", Bioconjugate Chem., 16: 1176-1180 (2005).
Dos Santos, Washington L.C. et al., "Control of lymphocyte adhesion to brain and aortic endothelium: ICAM-1, VCAM-1 and negative charge", Journal of Neuroimmunology, 66: 125-134 (1996).
East, Emma et al., "Engineering an Integrated Cellular Interface in Three-Dimensional Hydrogel Cultures Permits Monitoring of Reciprocal Astrocyte and Neuronal Responses", Tissue Engineering: Part C, 18(7): 526-537 (2012).
East, Emma et al., "A versatile 3D culture model facilitates monitoring of astrocytes undergoing reactive gliosis", J. Tissue Eng. Regen. Med., 3: 634-646 (2009).
Gannon, Christopher J. et al., "Intracellular gold nanoparticles enhance non-invasive radiofrequency thermal destruction of human gastrointestinal cancer cells", Journal of Nanobiotechnology, 6: 2 (2008).
Georgieva, Julia V. et al., "Surface Characteristics of Nanoparticles Determine Their Intracellular Fate in and Processing by Human Blood-Brain Barrier Endothelial Cells In Vitro", Molecular Therapy, 19(2): 318-325 (2011).
Gromnicova, Radka et al., "Glucose-Coated Gold Nanoparticles Transfer across Human Brain Endothelium and Enter Astrocytes in Vitro", PLOS One, 8(12): e81043 (2013).
Gu, Yan-Juan et al., "Nuclear penetration of surface functionalized gold nanoparticles", Toxicology and Applied Pharmacology, 237: 196-204 (2009).
Lund, Torben et al., "The influence of ligand organization on the rate of uptake of gold nanoparticles by colorectal cancer cells", Biomaterials, 32: 9776-9784 (2011).
Male, David, "Brain endothelium", Natural Cell Culture, eds. Cohen & Wilkin, pp. 121-130 (1995).
Male, Keith B. et al., "Assessment of Cytotoxicity of Quantum Dots and Gold Nanoparticles Using Cell-Based Impedance Spectroscopy", Anal. Chem., 80(14): 5487-5493 (2008).
Morgello, Susan et al., "The Human Blood0Brain Barrier Glucose Transporter (GLUT1) is a Glucose Transporter of Gray Matter Astrocytes", GLIA, 14: 43-54 (1995).
Wang, Yun-Yan et al., "Receptor-mediated therapeutic transport across the blood-brain barrier", Immunotherapy, 1(6): 983-993 (2009).
Weksler, B.B. et al., "Blood-brain barrier-specific properties of a human adult brain endothelial cell line", The FASEB Journal, 19: 1872-1875 (2005).
Huang, Shih-Hung et al., "Direct Binding and Characterization of Lipase onto Magnetic Nanoparticles", Biotechnol. Prog., 19: 1095-1100 (2003).
Vestal, Christy R. et al., "Effects of Surface Coordination Chemistry on the Magnetic Properties of MnFe2O4 Spinel Ferrite Nanoparticles", J. Am. Chem. Soc., 125: 9828-9833 (2003).
Neveu, S. et al., "Size-Selective Chemical Synthesis of Tartrate Stabilized Cobalt Ferrite Ionic Magnetic Fluid", J. Colloid and Interface Science, 255: 293-298 (2002).
Cao, YunWei Charles et al., "Nanoparticles with Raman Spectroscopic Fingerprints for DNA and RNA Detection", Science, 297: 1536-1540 (2002).
Rice, Peter et al., "EMBOSS: The European Molecular Biology Open Software Suite", Trends in Genetics, 16(6): 276-77 (2000).
Zhu, Jun et al., Development of a AU nanoparticles templates for PET in vivo imaging: 18F labeled 3 nm water-soluble AuNP cross the blood brain barrier, Abstracts of Papers American Chemical Society, 244, p. 485 (2012).
Invitation to Pay Additional Fees and, Where Applicable, Protest Fee with Annex to Form PCT/ISA/206—Communication Relating to the Results of the Partial International Search dated Apr. 23, 2014 in related International Application No. PCT/GB2014/050372.
Office Action, dated Nov. 28, 2017, issued in corresponding Japanese Application No. 2015-556568.
Zhu, Jun, "Development of a Au nanoparticles template for PET in vivo imaging: 18F labeled 3nm water-soluble AuNP cross the blood brain barrier", Abstracts of Papers of the American Chemical Society, vol. 244 (2012).
Office Action, dated Feb. 6, 2018, issued in Chinese Application No. 2014800191257.
English translation of Office Action, dated Feb. 6, 2018, issued in Chinese Application No. 2014800191257.

* cited by examiner

NANOPARTICLE DELIVERY COMPOSITIONS

FIELD OF THE INVENTION

The present invention relates to substances and compositions useful for delivery of agents to the central nervous system (CNS), in particular the delivery of biologically active agents across the blood-brain barrier (BBB). Substances, compositions and methods disclosed herein find use in the therapeutic and/or prophylactic treatment of disorders of the CNS, for imaging, targeting, repairing and studying the interaction of biologically active agents with, cells of the CNS.

BACKGROUND TO THE INVENTION

One of the major challenges for the pharmaceutical industry is drug delivery into the central nervous system (CNS). More than 95% of potentially useful drugs are prevented from entering the CNS due to the protective function of the blood-brain barrier, formed by microvascular endothelium and astrocytes. The key elements of the barrier are continuous tight-junctions between endothelial cells, which prevent molecules from diffusing into the brain, and ABC-transporters that actively pump xenobiotics out of the brain (1, 2). As a result, many drugs and larger biomolecules, including cytokines and genes which have considerable potential for the treatment of CNS disease, are excluded by the endothelial barrier (3-6).

Considerable efforts have been made to find a way of overcoming the blood-brain barrier, including the use of nanoparticles as a carrier (7). Biologically interesting nano- and micro-particles ranging from 1 nm to 500 nm have been made from materials such as polymers, lipids and metals, including gold. Gold nanoparticles have the advantage of easy production and chemical stability, and they have been recently used in nanomedicine for both diagnosis and therapy (8). The gold core is inert but it does interact with biological material and can have biological effects. To address this, a variety of sizes and surface modifications have been investigated which affect the specific behaviour of the nanoparticles (9-11). The transport into a cell is a property which can vary significantly depending on size and surface coating (12). Small-sized gold nanoparticles (>30 nm) are able to enter cells via an endocytic pathway (13, 14) although the mechanism of the transport is not exactly known. It is thought that gold nanoparticles do not enter the nucleus (15) unless the cell is apoptotic. In contrast, they are often trapped in vesicles (16-19) which can cause a problem for targeted drug/gene delivery into the cell and tissues in general.

Hence, focusing on the CNS and the blood-brain barrier, there remains an unmet need for a CNS nanoparticle-based molecular delivery, in particular exhibiting one or more of the following features:
1. Selectivity for the brain endothelium
2. Ability to cross the brain endothelium intact
3. Uptake by the target cell within the CNS.

The present invention addresses these and other needs.

BRIEF DESCRIPTION OF THE INVENTION

Broadly, the present invention relates to nanoparticle delivery systems for use in targeting biologically active or imaging agents to the central nervous system. The present inventors have found that nanoparticles, as defined herein, cross the endothelium and enter astrocytes. Moreover, the nanoparticles exhibit some selectivity for human brain endothelium, e.g. vs. non-brain endothelium. Biologically active agents may be coupled to nanoparticles, e.g. by means of covalent attachment via a linker, or reversibly bound to nanoparticles, e.g. by stably but reversibly binding to a nanoparticle corona. The agents are then delivered by the nanoparticles as "cargo" across the blood brain barrier to cells of the central nervous system, e.g. for therapeutic treatment of disorders of the central nervous system (CNS) or for imaging the CNS.

Accordingly, in a first aspect the present invention provides a nanoparticle composition for use in a method of delivering at least one agent to the central nervous system (CNS) of a mammalian subject, said composition comprising:
(a) a nanoparticle comprising:
 (i) a core comprising a metal and/or a semiconductor;
 (ii) a corona comprising a plurality of ligands covalently linked to the core, wherein said ligands comprise a carbohydrate, insulin and/or a glutathione; and
(b) the at least one agent to be delivered to the CNS.

In some cases, in accordance with the present invention, the composition is for use in a method of treatment of a CNS disorder of the subject.

In some cases in accordance with the present invention the composition is for use in a diagnostic or prognostic method of imaging of the CNS of the subject. Said method may be a method carried out on the body of the subject (in vivo).

In a second aspect the present invention provides a method for delivering at least one agent to the central nervous system (CNS) of a mammalian subject, said method comprising administering a composition to the subject, said composition comprising:
(a) a nanoparticle comprising:
 (i) a core comprising a metal and/or a semiconductor;
 (ii) a corona comprising a plurality of ligands covalently linked to the core, wherein said ligands comprise a carbohydrate, insulin and/or a glutathione; and
(b) the at least one agent to be delivered to the CNS.

In some cases in accordance with this aspect of the present invention the method is a method of treatment of a CNS disorder of the subject.

In some cases in accordance with this aspect of the present invention the method is a diagnostic or prognostic method of imaging of the CNS of the subject. Said method may be a method carried out on the body of the subject (in vivo).

In a third aspect the present invention provides use of a composition in the preparation of a medicament to be delivered to the central nervous system (CNS) of a mammalian subject, said composition comprising:
(a) a nanoparticle comprising:
 (i) a core comprising a metal and/or a semiconductor;
 (ii) a corona comprising a plurality of ligands covalently linked to the core, wherein said ligands comprise a carbohydrate, insulin and/or a glutathione; and
(b) at least one agent to be delivered to the CNS.

In some cases in accordance with this aspect of the present invention the medicament is for the treatment of a CNS disorder of a mammalian subject.

In some cases in accordance with this aspect of the present invention the medicament is for diagnostic or prognostic imaging of the CNS of the subject. Said diagnostic or prognostic imaging of the CNS of the subject may be carried out on the body of the subject (in vivo).

In some cases in accordance with the first, second and/or third aspect of the present invention, the composition is administered, or is for administration, via a non-central route, whereby said at least one agent is delivered across the blood-brain barrier to the CNS by association with said nanoparticle. In particular, the composition may be administered, or for administration, other than by intracerebral, intrathecal or epidural route. Suitable routes of administration include enteral (e.g. solid or liquid composition for ingestion); buccal; sublabial; sublingual; by inhalation; via a mucosal membrane; urogenital; rectal; dermal; and intradermal, intramuscular, intravenous, intraperitoneal, and subcutaneous injection or infusion.

In some cases in accordance with the first, second and/or third aspect of the present invention, the subject has an impaired or "leaky" blood-brain barrier. In particular, the subject may be suffering from a condition, such as a brain tumour or an infection, that renders the blood-brain barrier more permeable than would be the case in the absence of the condition.

In some cases in accordance with the first, second and/or third aspect of the present invention, the subject has a substantially functional blood-brain barrier (i.e. not leaky or impaired). In particular, the subject may be free from a condition that renders the blood-brain barrier more permeable than would be considered normal for the subject's species and age. Without wishing to be bound by any particular theory, the present inventors believe that the nanoparticles defined herein are capable of crossing a healthy blood-brain barrier and thereby delivering at least one agent to the CNS of the subject. This to be contrasted with the rather less challenging delivery of agents to the CNS of a subject suffering from a condition that renders the blood-brain barrier more permeable than would be the case in the absence of the condition.

In some cases in accordance with the first, second and/or third aspect of the present invention, the subject is a human.

As will be appreciated by the skilled person, the at least one agent for delivery to the CNS may be selected according to the desired biological (e.g. therapeutic, prophylactic, diagnostic or prognostic) effect to be achieved for the subject. In particular, the subject may have a CNS condition and the at least one agent may be therapeutically effective against said CNS condition. A wide variety of agents are contemplated for use in accordance with the present invention. Delivery of small molecule drugs, nucleic acids (e.g. vectors, RNAi), peptides (e.g. insulin, GLP-1, IGF1, IGF2, relaxin, INSL5, INSL6, INSL7, pancreatic polypeptide (PP), peptide tyrosine tyrosine (PTT), neuropeptide Y, oxytocin, vasopressin, GnRH, TRH, CRH, GHRH/somatostatin, FSH, LH, TSH, CGA, prolactin, ClIP, ACTH, MSH, enorphins, lipotropin, GH, calcitonin, PTH, inhibin, relaxin, hCG, HPL, glucagons, insulin, somatostatin, melatonin, thymosin, thmulin, gastrin, ghrelin, thymopoietin, CCK, GIP secretin, motin VIP, enteroglucagon, IGF-1, IGF-2, leptin, adiponectin, resistin Osteocalcin, renin, EPO, calicitrol, ANP, BNP, chemokines, cytokines, and adipokines, and biologically active analogues thereof), proteins (including cytokines and antibodies) to the CNS (e.g. to astrocytes) is expected to provide considerable flexibility of treatment options for therapeutic treatment of a wide range of CNS disorders. As used herein in connection with any aspect of the present invention a CNS disorder may be selected from the group consisting of: neoplasms (including brain tumours such as glioma, astrocytoma, primary brain tumours, secondary brain tumours as a result of metastasis of a primary tumour from elsewhere to the CNS); neurodegenerative disease (including Alzheimer's disease, multiple sclerosis, Parkinson's disease and Huntingdon's disease); stroke (ischaemic and haemorrhagic); neurological disorders (including epilepsy); infection (including viral, bacterial or parasitic encephalitis); immune disorders of the CNS (including autoimmune disorders); psychiatric disorders (including schizophrenia, depression and anxiety); genetic abnormalities (including inborn errors of metabolism); traumatic brain injury; coma; and developmental and learning disorders.

In a fourth aspect the present invention provides an in vitro screening method for identifying agents that are capable of being delivered across the blood-brain barrier to the central nervous system of a mammalian subject by association with a nanoparticle, said method comprising:
  providing a cell culture endothelium, optionally co-cultured with astrocytes;
  contacting the endothelium with a nanoparticle having associated with it at least one candidate agent; and
  identifying whether the candidate agent is delivered across the endothelium by the nanoparticle,
wherein said nanoparticle comprises:
  (i) a core comprising a metal and/or a semiconductor; and
  (ii) a corona comprising a plurality of ligands covalently linked to the core, wherein said ligands comprise a carbohydrate, insulin and/or a glutathione.

In a fifth aspect the present invention provides an in vivo screening method for identifying agents that are capable of being delivered across the blood-brain barrier to the central nervous system (CNS) of a mammalian subject by association with a nanoparticle, said method comprising:
  administering to a non-human mammalian test subject via a non-central route of administration a composition comprising a nanoparticle having associated with it at least one candidate agent; and
  identifying whether the candidate agent is delivered across the blood-brain barrier to the CNS of said test subject,
wherein said nanoparticle comprises:
  (i) a core comprising a metal and/or a semiconductor; and
  (ii) a corona comprising a plurality of ligands covalently linked to the core, wherein said ligands comprise a carbohydrate, insulin and/or a glutathione.

In some cases in accordance with any one of the aspects of the present invention, the at least one agent is be coupled to the nanoparticle, e.g. by covalent attachment (whether direct or via a linker) to the core of the nanoparticle. In some cases the at least one agent is reversibly (e.g. non-covalently) bound to the corona of the nanoparticle.

In some cases in accordance with any one of the aspects of the present invention, the at least one agent may be incorporated into the structure of the nanoparticle. For example, where the agent comprises a radionuclide (e.g. for targeting a brain tumour), the radionuclide may be present within the core of the nanoparticle.

The nanoparticles as defined herein, although small, have a significant surface area and are in many cases readily able to carry a cargo comprising a large number of agents and/or a mixture of different agents. Accordingly, in some cases in accordance with the present invention the nanoparticle has associated with it two or more (such as 2, 3, 4, 5, 6, 7, 8, 9, 10, 20, 50, 100 or more) entities of said agent (e.g. two or more molecules of a particular drug, two or more molecules of a particular nucleic acid or peptide or protein). In some cases in accordance with the present invention the at least one agent comprises two or more (such as 2, 3, 4, 5, 6, 7, 8, 9, 10 or more) different species of agent attached to different nanoparticles in the composition or attached to a common nanoparticle (a multi-functional nanoparticle). Advantageously, the different species of agent may exhibit co-operative behaviour or synergy in their biological effects. A particular example is the combination of two drugs for treatment of a specific CNS disorder where the two drugs act co-operatively.

In some cases in accordance with the present invention the ligands of the nanoparticle may be covalently linked to the core of the nanoparticle via a linker, such as a C2-C15 alkyl (e.g. C2, C3, C4, C5, C6, C7, C8, C9, C10, C11, C12, C13, C14 or C15, whether straight or branched-chain) and/or C2-C15 glycol (e.g. C2, C3, C4, C5, C6, C7, C8, C9, C10, C11, C12, C13, C14 or C15), e.g., a thioethyl group or a thiopropyl group.

In some cases in accordance with the present invention the ligands of the nanoparticle are covalently linked to the core via a sulphur-containing group, an amino-containing group, a phosphate-containing group or an oxygen-containing group.

In some cases in accordance with the present invention, the ligands comprise a carbohydrate which is a monosaccharide or a disaccharide. In particular, said carbohydrate moiety may comprise glucose, alpha galactose, mannose, fucose, maltose, lactose, galactosamine and/or N-acetylglucosamine.

In some cases in accordance with the present invention said ligands comprise 2'-thioethyl-$\beta$-D-glucopyranoside or 2'-thioethyl-$\alpha$-D-glucopyranoside covalently attached to the core via the thiol sulphur atom.

In some cases in accordance with the present invention said ligands comprise glutathione alone or in conjunction with other species of ligand, e.g., combinations of glutathione and carbohydrate ligands and/or insulin (including glucose-containing ligands) are specifically contemplated herein.

In some cases in accordance with the present invention, the nanoparticle comprises at least 1, 2, 3, 4, 5, 6, 7, 8, 9, 10, at least 20, at least 30, at least 40 or at least 50 carbohydrate-containing ligands, insulin-containing ligands and/or glutathione ligands.

In some cases in accordance with the present invention the diameter of the core of the nanoparticle is in the range 1 nm to 5 nm.

In some cases in accordance with the present invention the diameter of the nanoparticle including its ligands is in the range 3 nm to 20 nm, optionally 4 nm to 15 nm or 4 nm to 5 nm.

In some cases in accordance with the present invention the core comprises a metal selected from the group consisting of: Au, Ag, Cu, Pt, Pd, Fe, Co, Gd and Zn, or any combination thereof.

In some cases in accordance with the present invention the core is magnetic.

In some cases in accordance with the present invention the core comprises a semiconductor. In particular, the semiconductor may in some cases be selected from the group consisting of: cadmium selenide, cadmium sulphide, cadmium tellurium and zinc sulphide.

In some cases in accordance with the present invention the core is capable of acting as a quantum dot.

The present invention includes the combination of the aspects and preferred features described except where such a combination is clearly impermissible or is stated to be expressly avoided. These and further aspects and embodiments of the invention are described in further detail below and with reference to the accompanying examples and figures.

DETAILED DESCRIPTION OF THE INVENTION

Figure 1A:
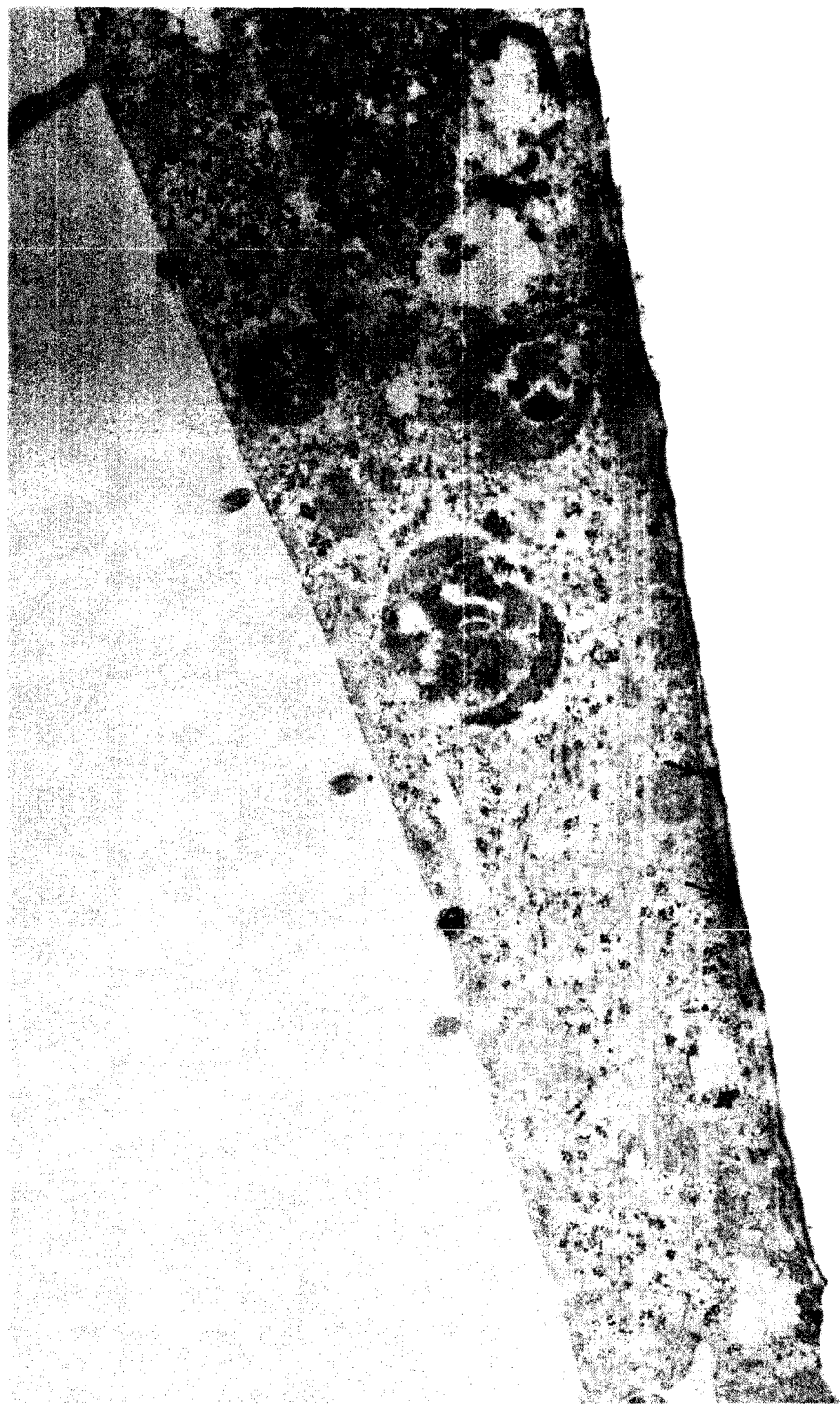
FIG. 1 shows electron micrographs of a) hCMEC/D3 cells and b) primary human brain endothelium 8 hours after application of glucose-nanoparticles to the apical surface. Nanoparticles are located between the basal plasma membrane and the basal lamina (arrows). Scale bar=500 nm.

In describing the present invention, the following terms will be employed, and are intended to be defined as indicated below.

As used herein, "nanoparticle" refers to a particle having a nanomeric scale, and is not intended to convey any specific shape limitation. In particular, "nanoparticle" encompasses nanospheres, nanotubes, nanoboxes, nanoclusters, nanorods and the like. In certain embodiments the nanoparticles and/or nanoparticle cores contemplated herein have a generally polyhedral or spherical geometry.

Nanoparticles comprising a plurality of carbohydrate-containing ligands have been described in, for example, WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticles may find use in accordance with the present invention. Moreover, gold-coated nanoparticles comprising a magnetic core of iron oxide ferrites (having the formula $XFe_2O_4$, where X=Fe, Mn or Co) functionalised with organic compounds (e.g. via a thiol-gold bond) are described in EP2305310 (the entire contents of which is expressly incorporated herein by reference) and are specifically contemplated for use as nanoparticles/nanoparticle cores in accordance with the present invention.

As used herein, "corona" refers to a layer or coating, which may partially or completely cover the exposed surface of the nanoparticle core. The corona includes a plurality of ligands which generally include at least one carbohydrate moiety, one surfactant moiety and/or one glutathione moiety. Thus, the corona may be considered to be an organic layer that surrounds or partially surrounds the metallic core. In certain embodiments the corona provides and/or participates in passivating the core of the nanoparticle. Thus, in certain cases the corona may include a sufficiently complete coating layer substantially to stabilise the semiconductor or metal-containing core. However, it is specifically contemplated herein that certain nanoparticles having cores, e.g., that include a metal oxide-containing inner core coated with a noble metal may include a corona that only partially coats the core surface. In certain cases the corona facilitates solubility, such as water solubility, of the nanoparticles of the present invention.

Nanoparticles

Nanoparticles are small particles, e.g. clusters of metal or semiconductor atoms, that can be used as a substrate for immobilising ligands.

Preferably, the nanoparticles have cores having mean diameters between 0.5 and 50 nm, more preferably between 0.5 and 10 nm, more preferably between 0.5 and 5 nm, more preferably between 0.5 and 3 nm and still more preferably between 0.5 and 2.5 nm. When the ligands are considered in addition to the cores, preferably the overall mean diameter of the particles is between 2.0 and 20 nm, more preferably between 3 and 10 nm and most preferably between 4 and 5 nm. The mean diameter can be measured using techniques well known in the art such as transmission electron microscopy.

The core material can be a metal or semiconductor and may be formed of more than one type of atom. Preferably, the core material is a metal selected from Au, Fe or Cu. Nanoparticle cores may also be formed from alloys including Au/Fe, Au/Cu, Au/Gd, Au/Fe/Cu, Au/Fe/Gd and Au/Fe/Cu/Gd, and may be used in the present invention. Preferred core materials are Au and Fe, with the most preferred material being Au. The cores of the nanoparticles preferably comprise between about 100 and 500 atoms (e.g. gold atoms) to provide core diameters in the nanometer range. Other particularly useful core materials are doped with one or more atoms that are NMR active, allowing the nanoparticles to be detected using NMR, both in vitro and in vivo. Examples of NMR active atoms include $Mn^{+2}$, $Eu^{+2}$, $Cu^{+2}$, $V^{+2}$, $Co^{+2}$, $Fe^{+2}$, $Fe^{+3}$ and lanthanides$^{+3}$, or the quantum dots described elsewhere in this application.

Nanoparticle cores comprising semiconductor compounds can be detected as nanometer scale semiconductor crystals are capable of acting as quantum dots, that is they can absorb light thereby exciting electrons in the materials to higher energy levels, subsequently releasing photons of light at frequencies characteristic of the material. An example of a semiconductor core material is cadmium selenide, cadmium sulphide, cadmium tellurium. Also included are the zinc compounds such as zinc sulphide.

In some embodiments, the core of the nanoparticles may be magnetic and comprise magnetic metal atoms, optionally in combination with passive metal atoms. By way of example, the passive metal may be gold, platinum, silver or copper, and the magnetic metal may be iron or gadolinium. In preferred embodiments, the passive metal is gold and the magnetic metal is iron. In this case, conveniently the ratio of passive metal atoms to magnetic metal atoms in the core is between about 5:0.1 and about 2:5. More preferably, the ratio is between about 5:0.1 and about 5:1. As used herein, the term "passive metals" refers to metals which do not show magnetic properties and are chemically stable to oxidation. The passive metals may be diamagnetic or superparamagnetic. Preferably, such nanoparticles are superparamagnetic.

Examples of nanoparticles which have cores comprising a paramagnetic metal, include those comprising $Mn^{+2}$, $Eu^{+2}$, $Cu^{+2}$, $V^{+2}$, $Co^{+2}$, $Ni^{+2}$, $Fe^{+2}$, $Fe^{+3}$ and $lanthanides^{+3}$.

Other magnetic nanoparticles may be formed from materials such as MnFe (spinel ferrite) or CoFe (cobalt ferrite) can be formed into nanoparticles (magnetic fluid, with or without the addition of a further core material as defined above. Examples of the self-assembly attachment chemistry for producing such nanoparticles is given in Biotechnol. Prog., 19:1095-100 (2003), J. Am. Chem. Soc. 125:9828-33 (2003), J. Colloid Interface Sci. 255:293-8 (2002).

In some embodiments, the nanoparticle or its ligand comprises a detectable label. The label may be an element of the core of the nanoparticle or the ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamine or tetramethyl rhodamine, Texas-Red, Cy3, Cy5, etc., and may be detected by excitation of the fluorescent label and detection of the emitted light using Raman scattering spectroscopy (Y. C. Cao, R. Jin, C. A. Mirkin, Science 2002, 297: 1536-1539).

In some embodiments, the nanoparticles may comprise a radionuclide for use in detecting the nanoparticle using the radioactivity emitted by the radionuclide, e.g. by using PET, SPECT, or for therapy, i.e. for killing target cells. Examples of radionuclides commonly used in the art that could be readily adapted for use in the present invention include $^{99m}Tc$, which exists in a variety of oxidation states although the most stable is $TcO^{4-}$; $^{32}P$ or $^{33}P$; $^{57}Co$; $^{59}Fe$; $^{67}Cu$ which is often used as $Cu^{2+}$ salts; $^{67}Ga$ which is commonly used a $Ga^{3+}$ salt, e.g. gallium citrate; $^{68}Ge$; $^{82}Sr$; $^{99}Mo$; $^{103}Pd$; $^{111}In$; which is generally used as $In^{3+}$ salts; $^{125}I$ or $^{131}I$ which is generally used as sodium iodide; $^{137}Cs$; $^{153}Gd$; $^{153}Sm$; $^{158}Au$; $^{186}Re$; $^{201}Tl$ generally used as a $Tl^{+}$ salt such as thallium chloride; $^{39}Y^{3+}$; $^{71}Lu^{3+}$; and $^{24}Cr^{2+}$. The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Additionally or alternatively, the nanoparticles of the present invention, or the results of their interactions with other species, can be detected using a number of techniques well known in the art using a label associated with the nanoparticle as indicated above or by employing a property of them. These methods of detecting nanoparticles can range from detecting the aggregation that results when the nanoparticles bind to another species, e.g. by simple visual inspection or by using light scattering (transmittance of a solution containing the nanoparticles), to using sophisticated techniques such as transmission electron microscopy (TEM) or atomic force microscopy (AFM) to visualise the nanoparticles. A further method of detecting metal particles is to employ plasmon resonance that is the excitation of electrons at the surface of a metal, usually caused by optical radiation. The phenomenon of surface plasmon resonance (SPR) exists at the interface of a metal (such as Ag or Au) and a dielectric material such as air or water. As changes in SPR occur as analytes bind to the ligand immobilised on the surface of a nanoparticle changing the refractive index of the interface. A further advantage of SPR is that it can be used to monitor real time interactions. As mentioned above, if the nanoparticles include or are doped with atoms which are NMR active, then this technique can be used to detect the particles, both in vitro or in vivo, using techniques well known in the art. Nanoparticles can also be detected using a system based on quantitative signal amplification using the nanoparticle-promoted reduction of silver (I). Fluorescence spectroscopy can be used if the nanoparticles include ligands as fluorescent probes. Also, isotopic labelling of the carbohydrate can be used to facilitate their detection.

Agents for Delivery to the CNS

A wide variety of agents are envisaged for delivery to the CNS using the products and methods of the present invention. Specifically contemplated are both: (i) agents that are known to enter the CNS, which may benefit from enhanced penetration of the BBB provided by the nanoparticles of the present invention (e.g. so that a lower dose may be administered while retaining therapeutic or imaging activity); and (ii) agents that have hitherto not been known to enter the CNS to an effective degree, which may provide new classes of therapeutic and imaging agents for targeting the brain (e.g. to expand available treatment modalities and diagnostic possibilities).

References herein to the "British National Formulary" refer to that version available November 2012 (see www.bnf.org).

Particular examples of agents that find use in accordance with the present invention include:

Hypnotics & Anxiolytics as referenced in the British National Formulary sub section 4.1 (the entire contents of which are expressly incorporated herein by reference) including but not limited to: loprazolam, lormetazepam, temazepam; zaleplon, zolpidem, zopiclone; clomethiazole; promethazine; melatonin; buspirone; Antipsychotics as referenced in the British National Formulary sub section 4.2 (the entire contents of which are expressly incorporated herein by reference) including but not limited to: chlorpromazine hydrochloride, haloperidol, perphenazine, prochlorperazine maleate or mesilate, promazine hydrochloride, trifluoperazine; clozapine, Olanzapine, quetiapine, risperidone.

Antimania medicines as referenced in the British National Formulary sub section 4.2 (the entire contents of which are expressly incorporated herein by reference) including but not limited to: carbamazepine and sodium valproate.

Antidepressants as referenced in the British National Formulary sub section 4.3 (the entire contents of which are expressly incorporated herein by reference) including but not limited to: amitriptyline hydrochloride, clomipramine hydrochloride, imipramine hydrochloride; mianserin hydrochloride; phenelzine, moclobemide; citalopram, fluoxetine, sertraline; agomelatine, flupentixol, tryptophan, venlafaxine.

Medicines to treat attention deficit hyperactivity disorder (ADHD) as referenced in the British National Formulary sub section 4.4 (the entire contents of which are expressly incorporated herein by reference) including but not limited to: atomoxetine, methylphenidate hydrochloride, modafinil.

Medicines used in the treatment of nausea and vertigo as referenced in the British National Formulary sub section 4.6 (the entire contents of which are expressly incorporated herein by reference) including but not limited to: cyclizine hydrochloride, chlorpromazine, droperidol, prochlorperazine maleate, metoclopramide hydrochloride, ondansetron, palonosetron, fosaprepitant, nabilone, betahistine dihydrochloride.

Medicines used for analgesia as referenced in the British National Formulary sub section 4.7 (the entire contents of which are expressly incorporated herein by reference) including but not limited to: nefopam hydrochloride; buprenorphine; diamorphine hydrochloride, fentanyl, meptazinol, tramadol hydrochloride; capsaicin; tolfenamic acid, zolmitriptan, pizotifen, clonidine.

Medicines used to treat epilepsy as referenced in the British National Formulary sub section 4.8 (the entire contents of which are expressly incorporated herein by reference).

Medicines used to treat Parkinsonism and related disorders as referenced in the British National Formulary sub section 4.9 (the entire contents of which are expressly incorporated herein by reference).

Medicines used to treat substance dependence as referenced in the British National Formulary sub section 4.10 (the entire contents of which are expressly incorporated herein by reference).

Medicines used to treat dementia as referenced in the British National Formulary sub section 4.11 (the entire contents of which are expressly incorporated herein by reference).

Medicines used in the treatment of astrocytoma's glioblastomas as referenced in the British National Formulary sub section 8 (the entire contents of which are expressly incorporated herein by reference) including but not limited to everolimus, temozolomide, carmustine.

Medicines used in the treatment of neurological disorders as referenced in the British National Formulary sub section 8.2.4 (the entire contents of which are expressly incorporated herein by reference) including but not limited to Glatiramer acetate, fingolimod.

Furthermore, classes of agent for delivery to the CNS in accordance with the present invention include: cytokines and nucleic acids, such as vectors for gene therapy.

Administration and Treatment

The nanoparticles and compositions of the invention may be administered to patients by any number of different routes, including enteral or parenteral routes. Parenteral administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes.

Administration be performed e.g. by injection, or ballistically using a delivery gun to accelerate their transdermal passage through the outer layer of the epidermis. The nanoparticles may also be delivered in aerosols. This is made possible by the small size of the nanoparticles.

The exceptionally small size of the nanoparticles of the present invention is a great advantage for delivery to cells and tissues, as they can be taken up by cells even when linked to targeting or therapeutic molecules. Thus, the nanoparticles may penetrate the brain endothelium and be internalised by cells such as astrocytes, their "cargo" of attached or associated agent(s) released, e.g., for interaction with CNS targets, such as glial or neuronal receptors, gene expression targets.

The nanoparticles of the invention may be formulated as pharmaceutical compositions that may be in the forms of solid or liquid compositions. Such compositions will generally comprise a carrier of some sort, for example a solid carrier or a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

In some cases the pharmaceutical composition may comprise a permeation enhancer. The permeation enhancer may, in some cases, be selected from an alkyl-D-maltoside and lysalbinic acid. The alkyl-D-maltoside may be selected from the group consisting of: hexyl-$\beta$-D-maltoside, octyl-$\beta$-D-maltoside, nonyl-$\beta$-D-maltoside, decyl-$\beta$-D-maltoside, undecyl-$\beta$-D-maltoside, dodecyl-$\beta$-D-maltoside, tridecyl-$\beta$-D-maltoside, tetradecyl-$\beta$-D-maltoside and hexadecyl-$\beta$-D-maltoside. In certain cases said alkyl-D-maltoside may comprise or consist of dodecyl-$\beta$-D-maltoside or tetradecyl-$\beta$-D-maltoside.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicising agent, preservative or anti-oxidant or other materials well known to those skilled in the art. Such materials should be non-toxic and should not interfere with the efficacy of the active ingredient. The precise nature of the carrier or other material may depend on the route of administration, e.g. intravenously, orally or parenterally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

Preferably, the pharmaceutically compositions are given to an individual in a prophylactically effective amount or a therapeutically effective amount (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Handbook of Pharmaceutical Additives, 2nd Edition (eds. M. Ash and I. Ash), 2001 (Synapse Information Resources, Inc., Endicott, N.Y., USA); Remington's Pharmaceutical Sciences, 20th Edition, 2000, pub. Lippincott, Williams & Wilkins; and Handbook of Pharmaceutical Excipients, 2nd edition, 1994. By way of example, and the compositions are preferably administered to patients in dosages of between about 0.01 and 100 mg of active compound per kg of body weight, and more preferably between about 0.5 and 10 mg/kg of body weight.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptoms of the disease.

As will be appreciated by the skilled person, the conditions for treatment by delivery of suitable agents to the CNS via nanoparticles as defined herein are many and varied. Such conditions include, without limitation, central nervous system disorders selected from the group consisting of: neoplasms (including brain tumours such as glioma, astrocytoma, primary brain tumours, secondary brain tumours as a result of metastasis of a primary tumour to the CNS); neurodegenerative disease (including Alzheimer's disease, multiple sclerosis, Parkinson's disease and Huntingdon's disease); stroke (ischaemic and haemorrhagic); neurological (including epilepsy); infection (including viral, bacterial or parasitic encephalitis); immune disorders of the CNS (including autoimmune disorders); psychiatric disorders (including schizophrenia, depression and anxiety); genetic abnormalities (including inborn errors of metabolism); traumatic brain injury; coma; and developmental and learning disorders.

The following is presented by way of example and is not to be construed as a limitation to the scope of the claims.

EXAMPLES

Example 1—Synthesis of Nanoparticles

Gold nanoparticles having a corona of glucose ligands or glutathione ligands were synthesised essentially as described previously (22), the entire contents of which is expressly incorporated herein by reference.

Briefly, the following general method was used to produce nanoparticles with gold metal cores of approx. 1.6 nm diameter, noting that the ligand coronas increase the hydrodynamic diameters to approx. 5 nm.

Oxidized ligand, either glutathione (Fluka 49741) or beta-2-mercaptoethoxy-glucose (synthesized in house), were dissolved in 9:1 methanol:water and gold III chloride (Sigma-Aldrich, Poole, UK) added. The organic ligands were used at a fourfold molar excess relative to the gold. The solution was then mixed for 5 min gently on a flat-bed shaker. The nanoparticles were produced by reduction following the rapid addition of a 20 fold molar excess relative to the gold, of freshly made 1 M sodium borohydride (Sigma-Aldrich, Poole, UK) under vigorous vortexing. The samples were vortexed for a total of 30 s followed by a further 1 h gentle mixing on the flat bed shaker. As the nanoparticles are not soluble in methanol/water solvent, initial purification was by bench centrifugation, supernatant removal and dispersion of the nanoparticle pellet in water. Further purification was achieved by 4 water washes in 10 kDa vivaspin centrifugation devices (GE Healthcare). The gold concentration of all nanoparticle preparations was determined by a simple colorimetric assay. Briefly 10 µl of nanoparticle sample or 12 mg/ml gold standard (Fluka (Sigma-Aldrich, Poole, UK)) and blanks were digested with 30 µl of 50:50 water:aqua regia in an ELISA plate for 1 min, this was followed by addition of 150 µl of 2 M NaBr, the 405 nm absorbance was then measured immediately, the assay having excellent linearity over the 0-10 µg range.

Example 2—Delivery of Nanoparticles Across an Endothelial Blood-Brain Barrier Model to Astrocytes The present inventors considered how selectivity for the CNS can be achieved. Since brain endothelium has a number of specific receptors and transporters which allow influx of nutrients into the brain, their ligands have been exploited in attempts to develop CNS specific nanoparticles (20). For example, nanoparticles coated with ApoE (targeting the LDL receptor) or OX26 antibody (targeting the transferrin receptor) have both been used in CNS drug delivery (16, 17). Another potential target is the glucose receptor (Glut-1), which is selectively expressed on brain endothelium and is also present on astrocytes (21).

In this study we focused on nanoparticles that can cross brain endothelium and enter the underlying astrocytes. We have used an in vitro model to examine the potential of glucose-coated gold nanoparticles to do so. The nanoparticles have a 2 nm gold core and 5 nm surface coating (22), a size which is considerably smaller than that used in related studies (16). These nanoparticles were chosen to enhance targeting for brain endothelium and astrocytes and to minimise endosomal uptake.

To investigate the distribution of gold nanoparticles in cells in vitro, we have used TEM to give quantitative information about localization of the nanoparticles in different subcellular compartments. Our study compares brain endothelium with endothelia from other tissues (bone marrow and coronary artery) in order to establish whether the glucose-coated nanoparticles are CNS-selective.

We have also investigated the rate of transport across brain endothelium and into astrocytes using a recently developed model of the blood brain barrier, in which human astrocytes are cultured in a 3-dimensional (3D) collagen gel, beneath a monolayer of human brain endothelium. The model is based on a 3D rat glial cell culture system developed in our laboratories (23, 24), which has been modified using primary human astrocytes and a brain endothelial cell line hCMEC/D3 (25). All cells used in this investigation are of human origin.

Materials and Methods

Endothelial Cell Cultures

Primary human brain microvessel endothelium was obtained from surgical resection, undertaken to treat epilepsy, with the informed consent of the patient. The cells were isolated from a small area of unaffected tissue at the tip of the temporal lobe, by collagenase/dispase digestion and isolation on BSA and percoll gradients as previously described (26). The cells were cultured (passage-1) on collagen-coated flasks or tissue culture inserts (Costar) in EBM-2 MV medium (Lonza) supplemented with 2.5% foetal bovine serum, hydrocortisone, VEGF, epidermal growth factor (EGF), insulin-like growth factor I (IGF-I), human fibroblast growth factor (FGF), ascorbic acid and gentamicin sulphate according to the manufacturer's formulation (Lonza), and penicillin/streptomycin (Invitrogen).

The human cerebral microvessel endothelial cell line hCMEC/D3 (25) at passage 24-30 and primary human coronary artery endothelial cells (hCAEC, Lonza; Cat. No. CC-2585) were cultured in EBM-2 medium. The human bone marrow endothelial cell line BMEC (27) was cultured in DMEM (Sigma) supplemented with 10% foetal bovine serum and 1% penicillin/streptomycin (Invitrogen). All the endothelial cells were cultured at 37° C. in a humidified atmosphere containing 5% $CO_2$, unless otherwise indicated.

3D Collagen Gel Astrocyte Cultures and Astrocyte/Endothelial Cocultures

Three-dimensional (3D) collagen gels were set up in a pre-warmed 24 well plate, with 450 µl of collagen mixture per well. The mixture contained 40% of rat tail collagen type I (5 mg/ml, dissolved in 0.6% acetic acid, First Link), 40% water, 10% of 10 times concentrated MEM and 10% suspension of human astrocytes ($1.2 \times 10^6$/ml passage 2-4). The gel was neutralized with sodium hydroxide immediately before the cell suspension was added. The gelation took ~10 min, then astrocyte medium (Sciencell) was added over the gel. Gels were cultured for 3 days before the nanoparticles were applied. In some cases, the astrocyte-gels were compressed using absorbers (TAP Biosystems) to approximately 10% of their original volume, before use.

For the astrocyte/endothelial cell cocultures, the astrocyte-containing gels were compressed for 15 min after 2 hours of incubation and were then cultured for 24 h in astrocyte medium before being overlaid with hCMEC/D3 cells at a cell density of 50000 cells/cm$^2$.

These co-cultures were incubated for 3 days in EBM-2, before the nanoparticles were applied to the apical surface in fresh media for 1, 3 or 8 hrs.

After the incubation with nanoparticles, the gels were washed ×3 in PBS and fixed in 2.5% glutaraldehyde in phosphate buffer for at least 1 hour. They were further processed for TEM, as described below for inserts.

Gold Nanoparticle Migration Assay

Gold nanoparticles (2 nm core) were synthesised by Midatech Ltd as described previously (22). In this study we used nanoparticles coated with glucose or glutathione. The glucose-coated nanoparticles have a diameter of ~4 nm and a mean molecular mass of ~27 kDa.

For transcytosis assays, 12-well collagen-coated inserts (Corning Costar) were seeded with 40000 cells/well and incubated for 2 or 3 days to reach confluency. The cells were then washed (HBSS) and gold nanoparticles (2 ng) were added to the fresh culture medium (0.5 ml) in the upper chamber. The cells were then incubated for 0-22 hrs at 37° C. Cells were washed three times in cold PBS to remove any loosely attached nanoparticles on the apical surface and were then fixed in 2.5% glutaraldehyde in phosphate buffer for at least 1 hour.

Transmission Electron Microscopy (TEM)

Silver enhancement (45 min, Aurion, UK) was used to help to visualise the nanoparticles. Post-fixation was carried out with 1% (w/v) osmium tetroxide in phosphate buffer for 1 hour and the filters were then washed in phosphate buffer for 10 min. The filters were taken out of the insert and randomly cut into 2 segments of 3-5 mm×2 mm. These segments were progressively dehydrated in 30-100% ethanol and finally embedded in Epon. Ultrathin sectioning was done with a Diatome diamond knife producing sections of 70-80 nm thickness, which were then loaded on copper grids coated with Pioloform. The grids were counterstained with uranyl acetate for 35 min, washed three times, immersed in lead citrate for 7 min and washed three times. The grids were observed on a transmission electron microscope JEM-1400 operated at an acceleration voltage of 80 kV using magnification of ×5000.

Sampling and Statistical Analysis of TEM Data

To choose representative data, a systematic sampling method was used. Twenty five pictures were taken from each section at regular intervals, i.e. every fourth microscopic field. If there was no cell in the fourth field or if the field contained an apoptotic cell, the stage was advanced until a viable cell was found. After this, every picture was analysed separately by counting the observed nanoparticles which were assigned into six categories (upper membrane, lower membrane, vesicular, intracytoplasmic, nuclear, junctional). In the vesicular category, we included all nanoparticles found in membrane-associated compartments excluding mitochondria. The membrane length visible in each picture (upper or lower membrane) was measured using software Image-J version 1.43. Data points are based on a measurement of at least 50 cells from each experimental treatment or time-point (2 technical replicates with 25 images per replicate). Each experiment was done 2-4 times and the figures show data from a representative experiment. The data is expressed either as nanoparticles per micron of plasma membrane or nanoparticles/cell, as appropriate. Note that the figures on the graphs refer to an 80 nm thick section of the cell, and estimates of the total number of nanoparticles/cell are made by calculation based on the area of the monolayers and the numbers of cells.

To evaluate astrocytes in 3D gels, pictures were taken of all astrocytes in each section; the area of each cell and nucleus was measured using Image-J and the nanoparticles counted and assigned to categories, as above.

For astrocytes in coculture with hCMEC/D3 cells in 3D gels, in each evaluated section of the gel, all astrocytes were counted, with a minimum sample size of 50 cells containing nanoparticles (>240 cells). The distance of each astrocyte from the basal membrane of the endothelium was also measured.

Results

Figure 1B:
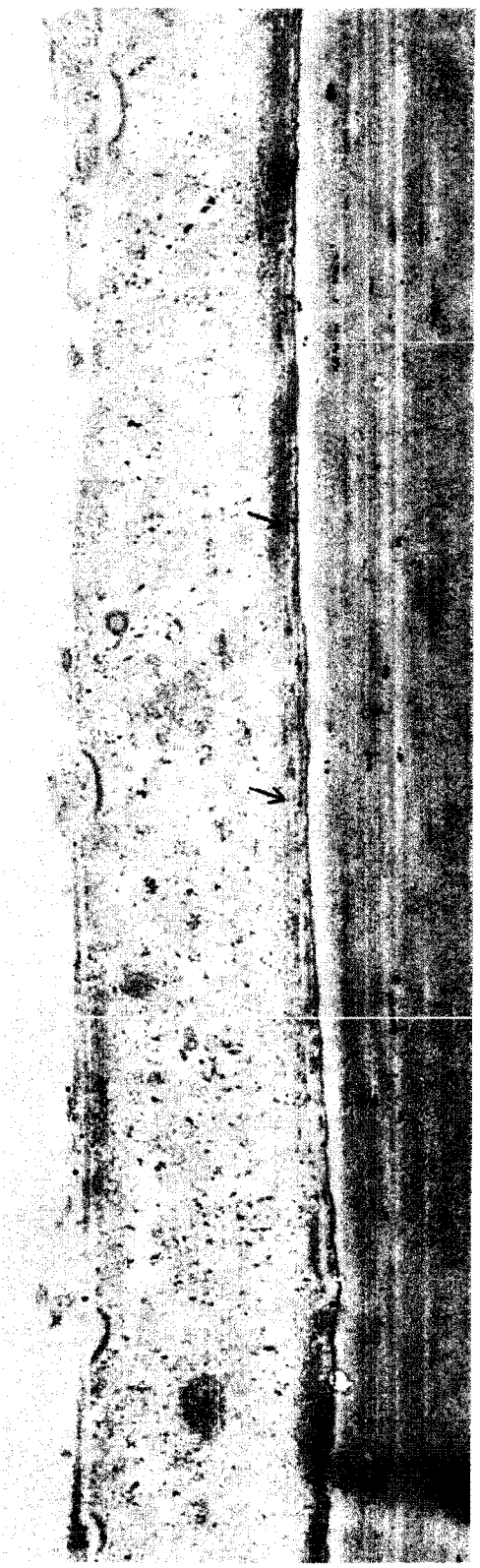

To determine whether glucose-coated nanoparticles can cross human brain endothelium, the nanoparticles were applied to the apical surface of endothelial cell monolayers. The cells were examined by silver-enhanced TEM after culture for 0-22 hours. The initial experiments were carried out with primary human brain endothelium (passage-1) or the brain endothelial cell line hCMEC/D3. The results showed that at 3-8 h, large numbers of nanoparticles were located between the basal plasma membrane and the collagen matrix on the supporting membrane (FIG. 1). At this time the nanoparticles were also present in the cytosol, but there were very few particles in vesicles or the nucleus or in intercellular junctions. The presence of nanoparticles in the cytosol and their absence from intercellular junctions suggested that they were directly crossing the cells by transcytosis, and were not reaching the basal membrane by paracellular movement.

Figure 2A:
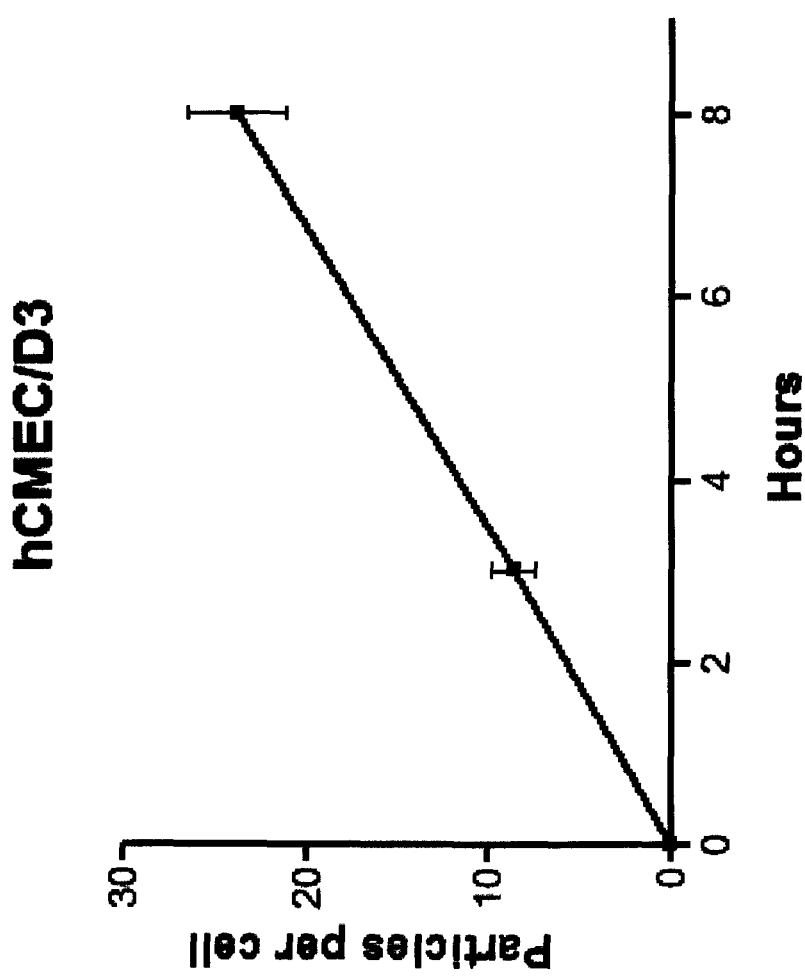
FIG. 2: shows graphs of the rate of transcytosis of 5 nm glucose-coated gold nanoparticles across a) hCMEC/D3 cells, b) a human bone marrow endothelial cell line (BMEC), and primary cultures of c) human brain endothelium or d) coronary artery endothelium. The values show the number of nanoparticles per cell, located between the basal plasma membrane and the basal lamina after application to the apical surface. Values show mean±SEM from at least 50 different cells, and two separate cultures. Note that the scale of the y-axis is expanded for the two non-brain endothelial cell types. e) shows a bar chart of the number of nanoparticles per micron (mean±SEM) in 80 nm sections from the four different cell types.
Figure 2B:
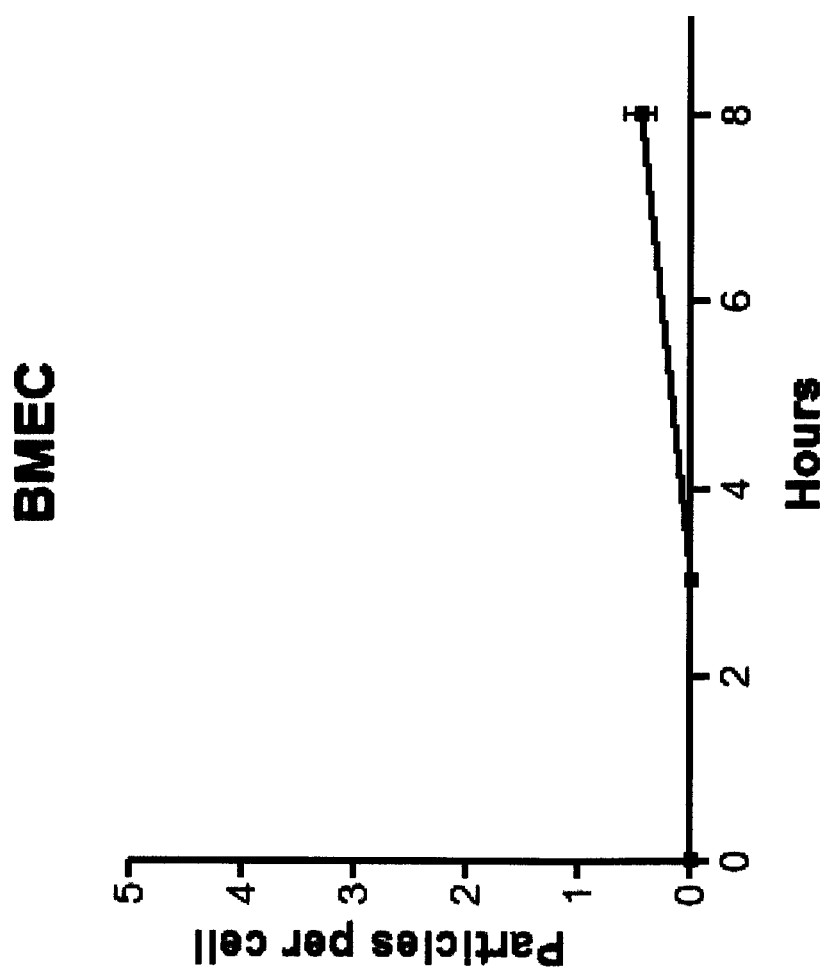
Figure 2C:
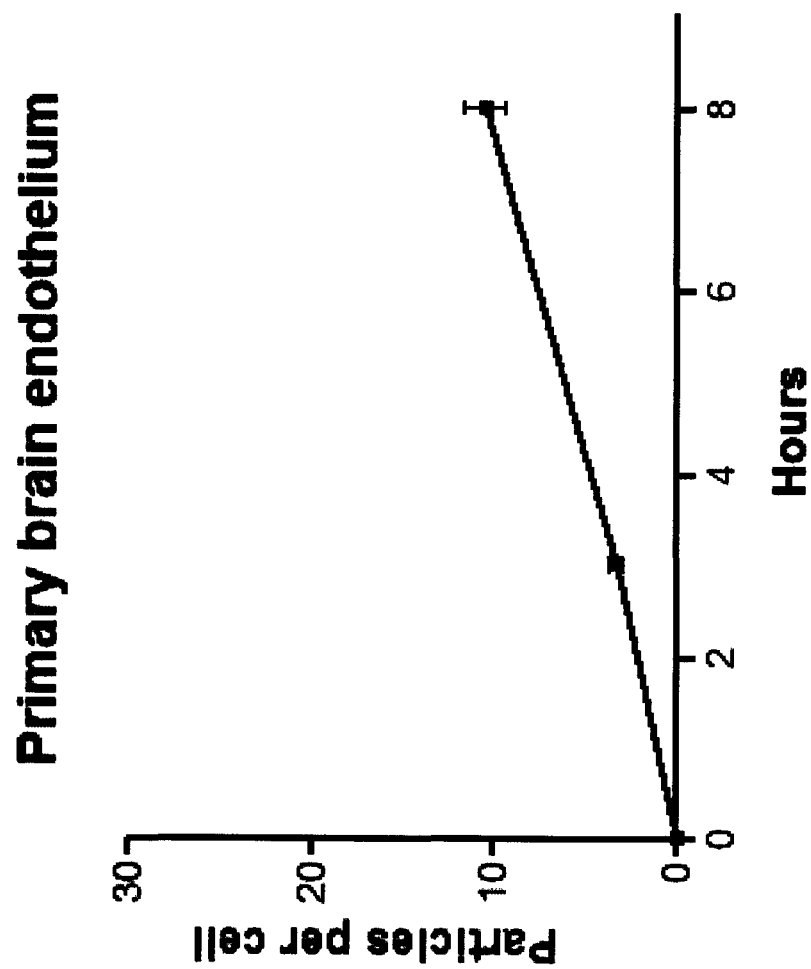
Figure 2D:
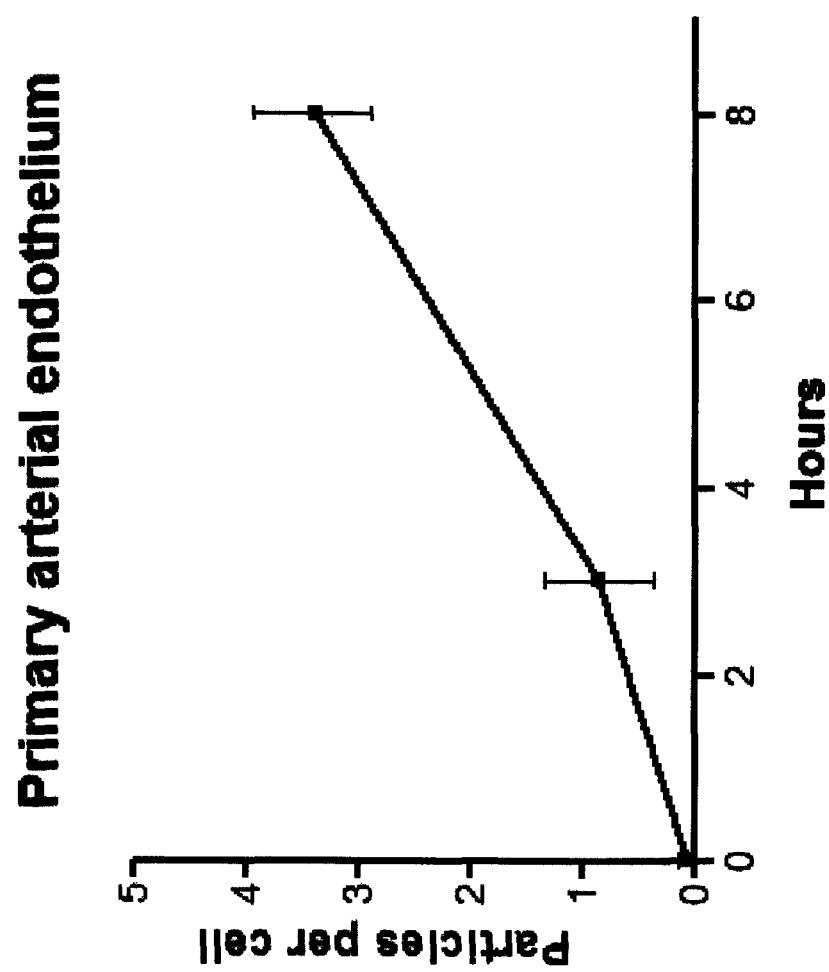
Figure 2E:
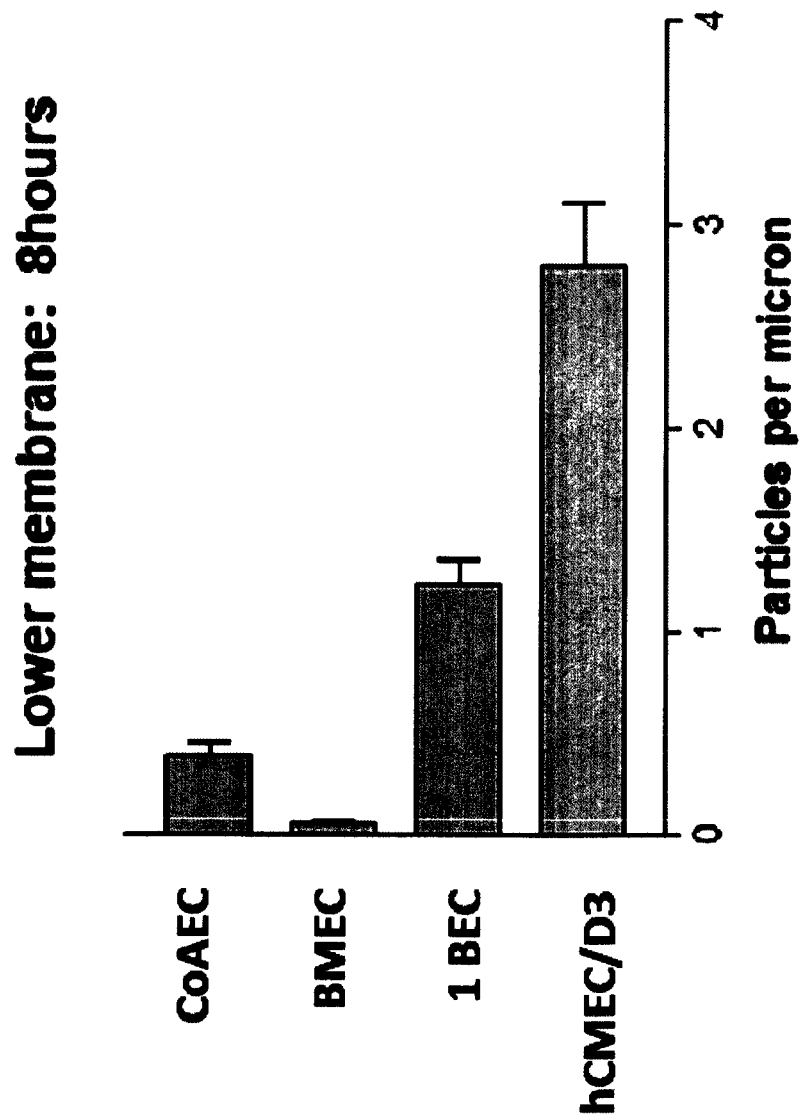

To determine the rate of transport in endothelia from different tissues, we compared the two brain endothelia with primary coronary artery endothelium and a bone marrow endothelial cell line BMEC (immortalised in a similar way as hCMEC/D3 cells). The rate at which nanoparticles cross the endothelium was determined by counting the number of nanoparticles located beneath the basal plasma membrane. Transcytosis of the brain endothelial cell line and the primary brain endothelium was approximately linear over 8 hours (FIG. 2a). Moreover, transfer across the two brain endothelial lines was considerably faster than across the two non-brain cell lines (FIG. 2e).

As an additional control, we used a non-endothelial cell type, human fibroblasts, in which the rate of movement of the nanoparticles was measured over 5 h, using the same experimental setup as above. The rate of transfer to the lower membrane of fibroblasts was <3% of the rate of transfer across the primary brain endothelium.

To estimate the percentage of applied nanoparticles that cross the endothelium, we counted all of the cell-associated nanoparticles in strips across two filters of hCMEC/D3 cells (>18,000 NPs) and calculated that $7 \times 10^9$ nanoparticles would be detectable in the entire area of the filter. We estimated that $4.4 \times 10^{10}$ nanoparticles were applied to each filter (2 ng), hence this represents ~16% of the applied nanoparticles. It should be noted that this is a minimum figure, since it does not take account of losses within the system or failure to detect some of the nanoparticles by TEM. Confluent monolayers of hCMEC/D3 cells on these filters typically contain ~$10^5$ cells, so the uptake is >$7 \times 10^4$ nanoparticles per cell.

Figure 3A:
FIG. 3 shows a) an electron micrograph of hCMEC/D3 cell 3 hours after application of glucose-NPs to the apical surface. The nanoparticles cross to the basal plasma membrane and are also seen in the cytosol and vesicles. Only one nanoparticle is detected in the intercellular junction (black arrow). Nanoparticles are also present in the pore in the supporting membrane (white arrow). b) Localisation of nanoparticles in hCMEC/D3 cells, primary brain endothelium (BEC) and coronary artery endothelium (CoAEC) 3 hours after application. Cy=cytoplasmic, Ves=vesicular, BM=basal membrane.
Figure 3B:
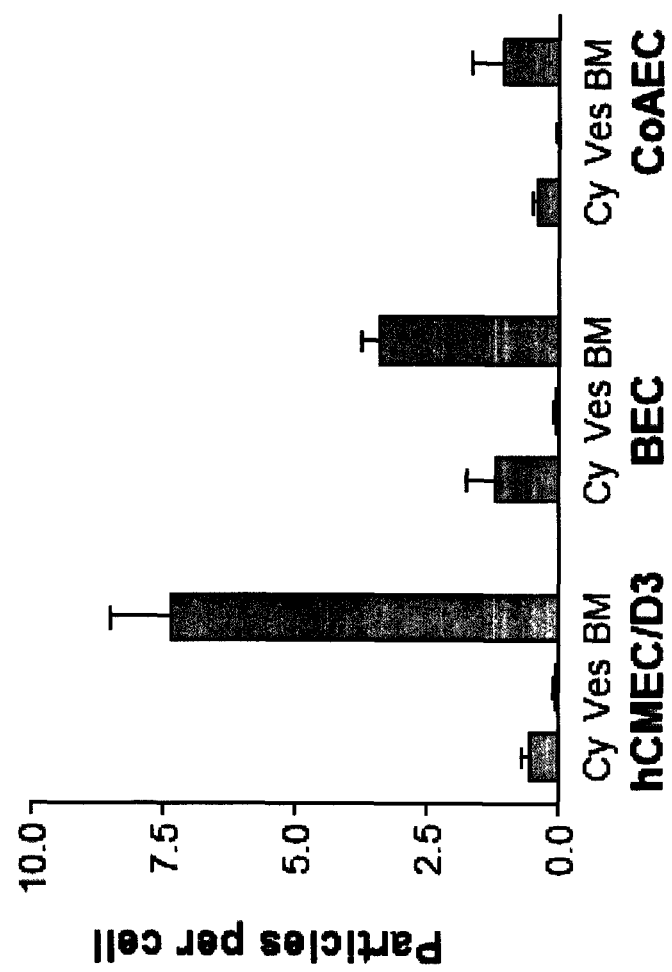

In other studies that have used nanoparticles in vivo or on brain endothelium in vitro, the particles have been predominantly localised to vesicles (16-18). However, these studies have generally used much larger nanoparticles. We therefore undertook a more careful analysis of subcellular localisation in order to understand the mechanism by which the nanoparticles cross the endothelium. We quantitated the numbers of particles seen in the cytosol, vesicles (i.e. endosomes and any other membrane associated structure excluding mitochondria), the nucleus and particles associated with the apical and basal plasma membranes. It was notable that nanoparticles were only occasionally seen in the intercellular junctions (FIG. 3a) or the cell nuclei. At 3-8 hours on all endothelial cells, the majority of the intracellular nanoparticles were seen in the cytosol, with a smaller proportion in the vesicles (FIG. 3b). We did observe nanoparticles in vesicles of hCMEC/D3 cells at 22 h (data not shown) but at this time, the particles were in clumps and there were fewer at the basal membrane. Hence, in the early stages (3-8 h) the nanoparticles appeared to cross the endothelium by non-vesicular transcytosis, but at the last time-point (22 h) they had become aggregated and were then located in endosomes.

Figure 4:
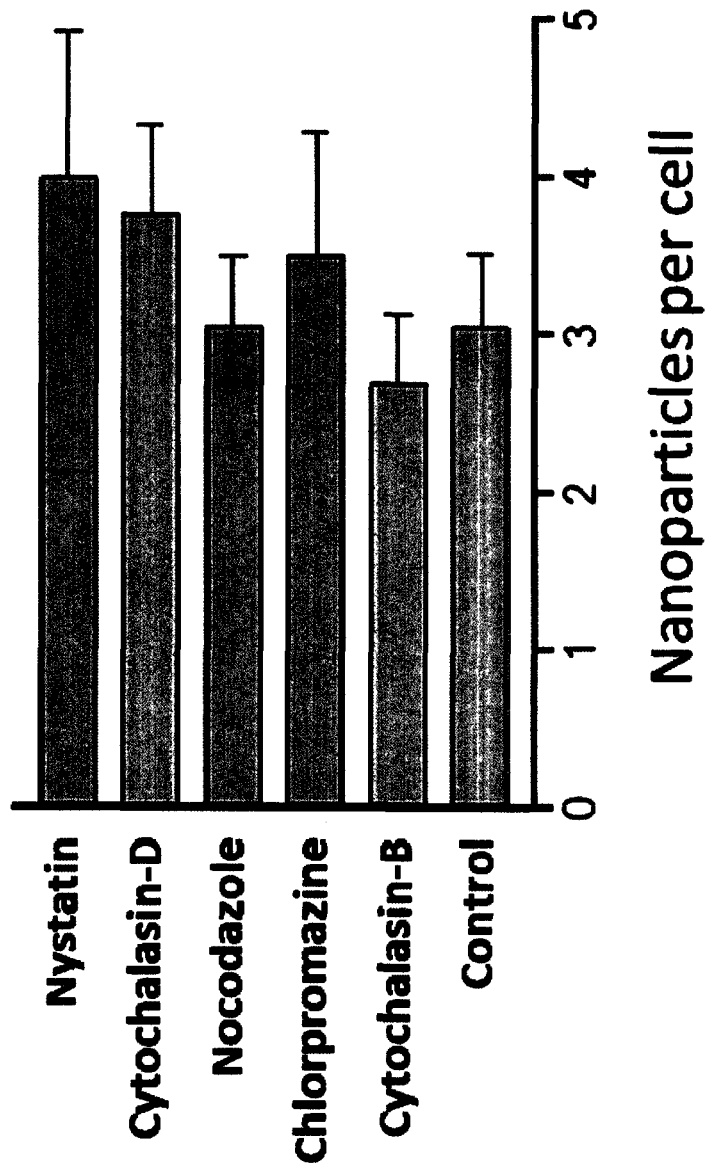
FIG. 4 shows representative experiment of the effect of antibiotics on transcytosis of glucose-nanoparticles across hCMEC/D3 cells. Data is expressed as the number of nanoparticles located at the basal membrane compared with untreated cells (control). Values are the mean±SEM of >50 cells. ANOVA indicates no significant difference between treatments.

To further investigate how the nanoparticles were moving across the cells experiments were carried out for 3 hours using hCMEC/D3 cells in the presence of antibiotics that interfere with endocytosis and/or vesicular transport—cytochalasin-B (glucose transport) chlorpromazine (clathrin-coated vesicles), nocodazole (microtubules), cytochalasin-D (microfilaments) and nystatin (caveolae and lipid rafts). In theory, if the nanoparticles are transported by a particular cellular system then antibiotic treatment should block transcytosis. (Preliminary experiments confirmed that the antibiotic doses used were not toxic for the cells for up to 5 h.) The results showed that at 3 h none of the treatments reduced the rate of nanoparticle transcytosis (FIG. 4). Therefore one possible mechanism for the transport of nanoparticles across the plasma membrane is by a passive diffusion. If this is correct then it would be in agreement with the observation that these nanoparticles cross via the cytosol, rather than by vesicles.

Figure 5:
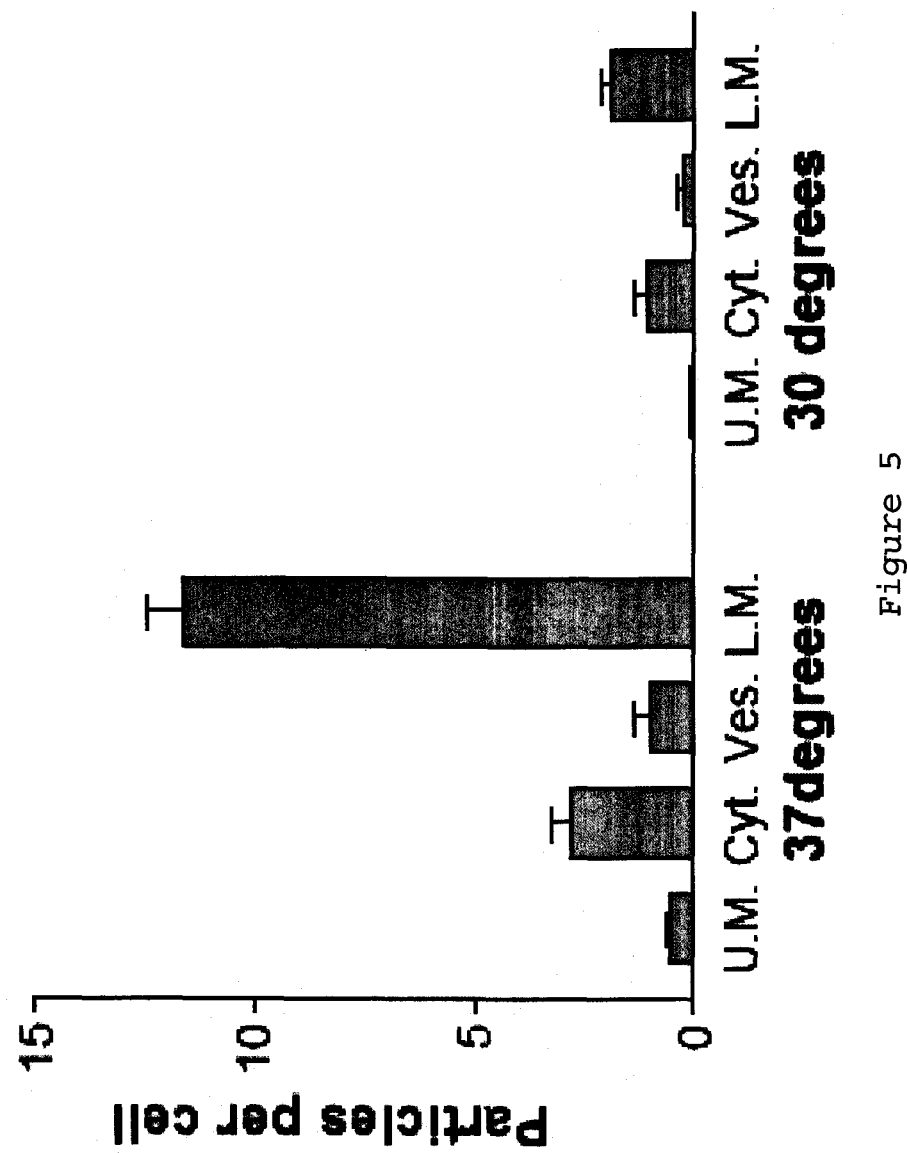
FIG. 5 shows the location of nanoparticles in hCMEC/D3 cells at 8 hours after application following incubation at 37° C. or 30° C. U.M.=Upper membrane, Cyt.=cytoplasmic, Ves.=vesicular, L.M.=lower membrane. The values are the mean±SEM from at least 50 TEM images from a representative experiment.

Since the apical and basal plasma membranes limit free diffusion of hydrophilic molecules, we reasoned that changing membrane fluidity might affect the rate of transcytosis To determine whether membrane fluidity could affect the rate of transcytosis, we compared cells at 37° C. and 30° C., a temperature which reduces fluidity (FIG. 5). At 30° C. transcytosis was <20% of the rate at 37° C. While this result is indicative it is not conclusive because the reduced temperature could also affect other relevant metabolic processes. Interestingly though the intracellular distribution of nanoparticles between subcellular compartments was unchanged at the lower temperature, which suggests a passive process. Also it is notable that reducing the temperature causes a very substantial decrease in transcytosis (lower membrane), presumably because the nanoparticles must cross two plasma membranes.

Figure 6:
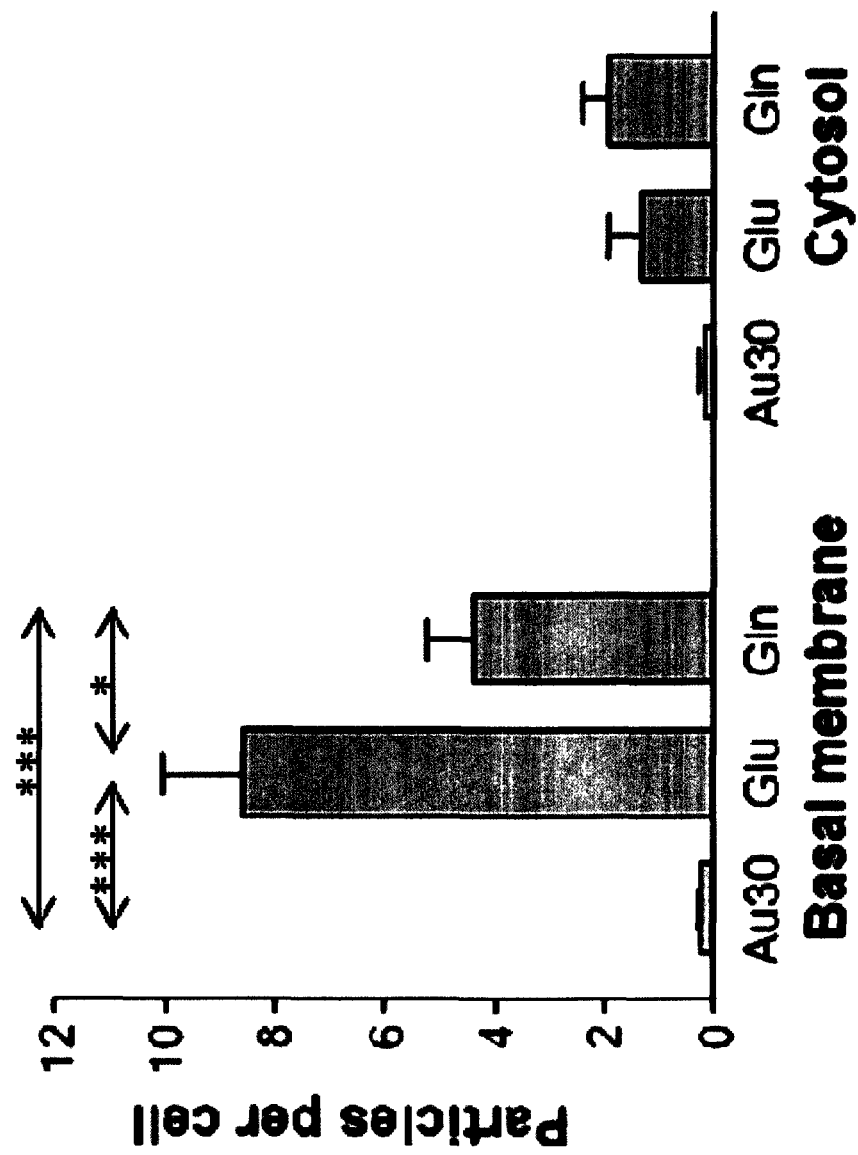
FIG. 6 shows a comparison of the rate of transcytosis of 30 nm colloidal gold (Au30), 4 nm glucose-coated nanoparticles (Glu) and 4 nm glutathione-coated nanoparticles (Gln) 22 hours after application to hCMEC/D3 cells. Values represent mean±SEM of the number of nanoparticles located beneath the basal plasma membrane or in the cytosol, based on at least 50 TEM images. Data was analysed by ANOVA ($P<0.01$ for the basal membrane), followed by a two-tailed t-test. * $P<0.05$, *** $P<0.001$.

The original rationale for the use of glucose-coated nanoparticles was that they could be carried by the Glut-1 transporter. However the failure to block uptake with cytochalasin-B (FIG. 4), suggested that active transport via this receptor was not taking place. To investigate the role of the coating we compared the rate of transcytosis of glucose-coated, and glutathione-coated 4 nm nanoparticles across hCMEC/D3 cells (FIG. 6). As an additional control for size dependence, 30 nm colloidal gold nanoparticles were also tested. Glucose-coated particles transcytosed more effectively than glutathione-coated nanoparticles and both 4 nm nanoparticles were more effective than the 30 nm colloidal nanoparticles. This result suggests that the characteristics of the nanoparticle, including its size, ligand and charge, all contribute towards the effectiveness of the transfer.

The ultimate aim of the project was to determine whether the nanoparticles could act as a carrier across the blood-brain barrier and target glial cells. In the initial experiments we had noted that the nanoparticles accumulated between the basal plasma membrane of the endothelium and the membrane of the insert. Moreover, the nanoparticles were also seen moving through the pores (220 nm) in the filters (see FIG. 3a), which indicated that they could be released by the endothelium and potentially enter the interstitial spaces.

Figure 7A:
FIG. 7 shows a) TEM of primary human astrocytes in a 3D collagen gel 8 hours after application of nanoparticles to the gel surface. Nanoparticles are visible both in the gel matrix and the astrocytes (arrows). b) TEM of astrocyte/endothelial coculture 8 hours after application of glucose-coated nanoparticles to the endothelial surface. Nanoparticles are detected both in the endothelium and the astrocyte (arrows). Small tears in the gel matrix are sometimes produced during the sectioning, by the presence of nanoparticles (white arrow).
Figure 7B:

To assess the potential of the nanoparticles to target glial cells we used a novel coculture system, in which human astrocytes were cultured in a 3D collagen gel, overlaid with a monolayer of brain endothelium (hCMEC/D3). Preliminary experiments (TEM) confirmed that the nanoparticles could pass freely through the gel matrix and enter the astrocytes (FIG. 7a). The nanoparticles were then applied on the endothelium in coculture and the rate of accumulation in astrocytes was measured over 1-8 hours. Observations were made from sufficient number of cells, to include at least 50 astrocytes containing nanoparticles (FIG. 7b). Over the 8 hour time course there was a progressive increase in the percentage of astrocytes with detectable nanoparticles (Table 1).

TABLE 1

Accumulation of nanoparticles in astrocytes in coculture

| Time[1] | Cells[2] | % Positive cells[3] | Distance[4] | Particles/cells[5] |
|---|---|---|---|---|
| 1 hour | 411 | 7.4 ± 2.0 | 10.6 ± 1.6 | 3.53 ± 0.41 |
| 3 hours | 308 | 15.9 ± 1.0 | 16.7 ± 2.6 | 4.16 ± 0.46 |
| 8 hours | 240 | 19.5 ± 0.6 | 15.5 ± 1.4 | 3.75 ± 1.15 |

[1]Time after application of nanoparticles to the apical surface of the endothelium.
[2]Total number of astrocytes observed.
[3]Percentage of astrocytes with intracellular nanoparticles.
[4]The distance in μm of each astrocyte containing nanoparticles from the basal surface of the endothelium.
[5]Number of nanoparticles observed in cells containing nanoparticles.

Within the 3D gel matrix, astrocytes containing nanoparticles are positioned at different depths from the endothelial monolayer and it was possible to detect the spread of nanoparticles to deeper astrocytes over 1-3 hours, although the numbers of particles detected per cell was similar at all times (Table 1). The thickness of the compressed gels is 40-60 μm. Therefore the observation that the median distance of nanoparticles from the endothelium at 3 hours was 16.7 μm, suggests that the nanoparticles can permeate the entire gel depth by this time. Since these observations, based on 80 nm thick sections, detected on average 3.75 nanoparticles/cell at 8 hours, we infer that a single astrocyte, which may be up to 80 μm in depth could contain several hundred nanoparticles. Hence 4 nm glucose-coated nanoparticles show great potential for selective uptake and transcytosis by brain endothelium and as carriers for delivery of therapeutic agents to astrocytes.

Discussion

Targeted delivery of drugs to cells of the CNS, is a major obstacle in the treatment of many diseases. Gold nanoparticles have considerable potential as carriers of therapeutic agents across the blood-brain barrier, as they are not immunogenic and smaller nanoparticles (3-5 nm) are not cytotoxic except at high doses (27, 28, 29). Here we show that 4 nm glucose-coated gold nanoparticles can cross brain endothelium with no detectable damage to the endothelial cells (33).

In this study, glucose-coated nanoparticles were selected because of their potential to bind to the glucose receptor, Glut-1, on brain endothelium and astrocytes. The finding, that these nanoparticles were selectively transported by brain endothelium (FIG. 2), initially supported the view that uptake or transcytosis was ligand-dependent. However transcytosis was not blocked by antibiotics that interfere with transport (FIG. 4), and altering the concentration of glucose in the medium also had no effect on transcytosis (data not shown). Hence it appears that transcytosis is not dependent on the glucose transporter system, and the physical configuration of the glucose coating makes it unlikely that it could engage the glut-1 receptor. As an alternative, it is possible that the initial attachment to the endothelium depends on the biophysical properties of the nanoparticles and the cells. In this respect, it is known that the glycocalyx of brain endothelium is highly sialylated, and quite different from endothelium in other tissues (30), which could explain the selective uptake by brain endothelium. It is likely that the size and composition of the nanoparticles is also important. We found that 30 nm nanoparticles and glutathione-coated 4 nm gold nanoparticles were both significantly less efficient at crossing the endothelium (FIG. 6).

Other studies have indicated that transcytosis of nanoparticles is an active process due to decreased uptake of nanoparticles into cells at 4° C. (31). Indeed, in one experiment (data not shown) we also found that no transcytosis occurred at 4° C. However, these studies did not take into consideration the fluidity of the plasma membrane which we propose could be a critical factor controlling the transmembrane movement of small nanoparticles.

As we were using a static in vitro culture, we considered the possibility that diffusion around the edge of the well or sedimentation should be taken into account. However, in the case of small sized gold nanoparticles, under 15 nm, these effects are negligible and should not have an effect on the transport mechanism (32). The absence of nanoparticles in the intercellular junctions also confirms that they do not use a paracellular route across the endothelium.

In the cocultures we cannot completely refute the idea of passive diffusion of nanoparticles into the gel round the edges of the cultures. However, as the number of nanoparticles increases substantially with the distance travelled from the endothelial monolayer over 1-3 hours (Table 1), this is most readily explained by movement of the nanoparticles from the basal lamina of the endothelium into the gel matrix and thence into the astrocytes.

The localisation of nanoparticles provided most interesting data. It was notable that nanoparticles were rarely seen in the nuclei of the endothelium, but common in the nuclei of astrocytes, either in single cell cultures or cocultures (FIG. 7). It is possible that changes in the surface coating of the nanoparticles occur during the extended period of the coculture, or as the particles cross the endothelium, which means that they subsequently tend to localise to the astrocyte nucleus. Currently the reason for this difference in subcellular localisation is obscure. Regardless of the mechanism, it is important that the nanoparticles are not trapped in the endothelium, if they are to be used to deliver a therapeutic cargo to cells of the CNS.

The number of transcytosed nanoparticles is also an important consideration. Our calculations suggest that >70,000 nanoparticles cross each endothelial cell and several hundred accumulate in each astrocyte. They therefore have the potential to carry an effective dose of a toxic agent, a receptor agonist or a gene to the target cells, if the process can be made to occur at a similar level in vivo. In short, 4 nm glucose-coated gold nanoparticles are selective for brain endothelium and they have great potential for delivery of therapeutic agents to target cells in the CNS.

Example 3—Delivery of Agents to the CNS

Agents, including small molecule drugs, labels and/or biological agents such as peptides or nucleic acids may be coupled to the nanoparticles as defined herein using essentially any suitable technique. Agents may be covalently linked to the core of the nanoparticle or may form a binding interaction with the corona of the nanoparticle. In particular, a label, e.g. an MRI contrast agent, such as a lanthanide may be complexed by carbohydrate groups present as ligands attached to the nanoparticle core (see, for example, Example 3 of WO 2004/108165, the entire contents of which are expressly incorporated herein by reference). Alternatively or additionally, one or more peptides or proteins (including for example cytokines, antibodies or neuropeptides) may be non-covalently bound to the corona of the nanoparticle (see, e.g., Example 3 of WO 2011/154711, the entire contents of which are expressly incorporated herein by reference). Alternatively or additionally, a nucleic acid such as an siRNA or a segment of DNA or RNA may be covalently linked to the core of the nanoparticle via thiol derivatisation of the nucleic acid at the 3' or 5' terminus of the nucleic acid strand (see, for example, WO 2005/116226, in particular the examples thereof, the entire contents of which are expressly incorporated herein by reference).

Delivery of agents to the CNS utilising nanoparticles as defined herein may be assessed using a model of the blood brain barrier as described in detail in Example 2. In some cases, assessment of successful delivery of the agent of interest to a CNS cell, such as an astrocyte, may involve physically identifying the presence of the agent (optionally together with the nanoparticle) in the target cell and/or performing a functional assay of the effect of said agent on the target cell. By way of example, where the agent comprises siRNA that targets a specific gene, a suitable functional assay may comprise assessment of expression of said gene in the target CNS cell. Preferably, one or more controls such as nanoparticles in the absence of the agent and/or agent in the absence of the nanoparticles will be contacted to the blood brain barrier model system thereby providing a reference against which the presence and/or effect of the nanoparticle having a cargo of the agent of choice is assessed.

Example 4—Nanoparticle Coatings and Transfer Across the Brain Endothelium

Figure 8:
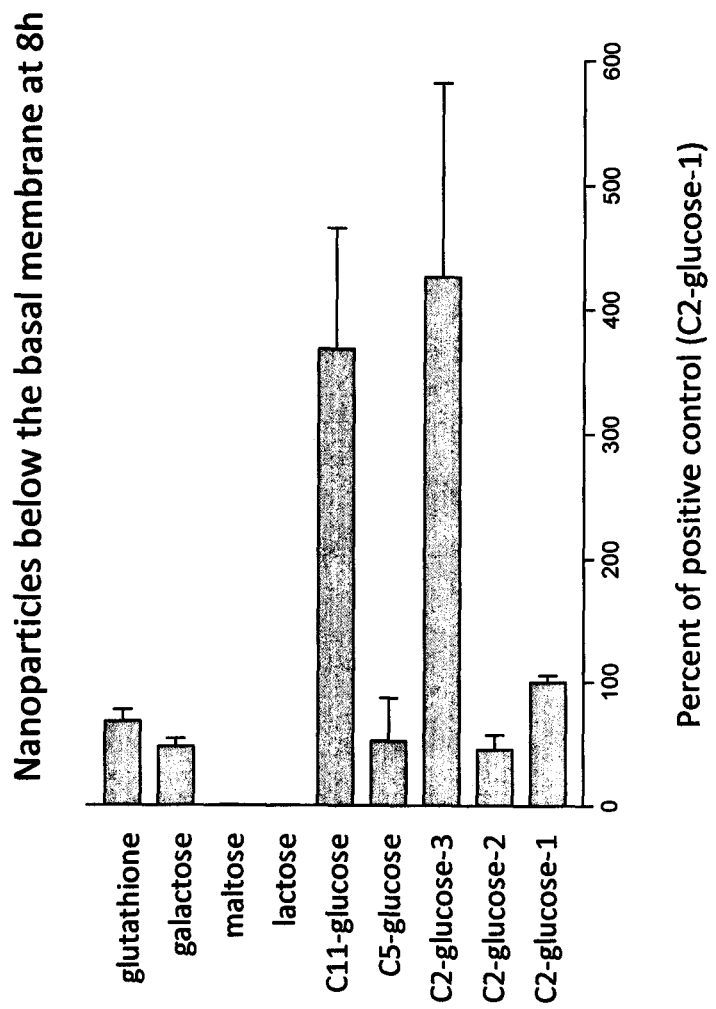
FIG. 8 shows the number of nanoparticles detected below the basal membrane at 8 hours plotted for each nanoparticle ligand species as a percentage of the control designated the C2-glucose-1.

The present study set out to investigate the following aims:
To determine whether gold nanoparticles with various surface coatings cross human brain endothelium.
To determine if transport can be selective for brain endothelium.
To investigate potential mechanisms of transfer and optimise the delivery system.
To determine whether nanoparticles can target glial cells after transfer across the endothelium.
To this end, nanoparticles having a corona comprising one or more of the following ligand species were synthesised essentially as described in Example 1:
C2-glucose
C5-glucose
C11-glucose
Maltose
Lactose
Galactose
Galactosamine
Glutathione The transfer rate of nanoparticles was found to vary according to the composition of the nanoparticle corona (i.e. the coating) and variation was seen between batches of nanoparticles (see FIG. 8). In particular the number of nanoparticles detected below the basal membrane at 8 hours is plotted for each nanoparticle ligand species as a percentage of the control designated the C2-glucose-1 (i.e. a first batch of nanoparticles having a glucose ligand corona with a C2 linker). It is clear that C11-glucose and a third batch of glucose (C2-glucose-3) exhibit greater than control transfer rate.

Figure 9:
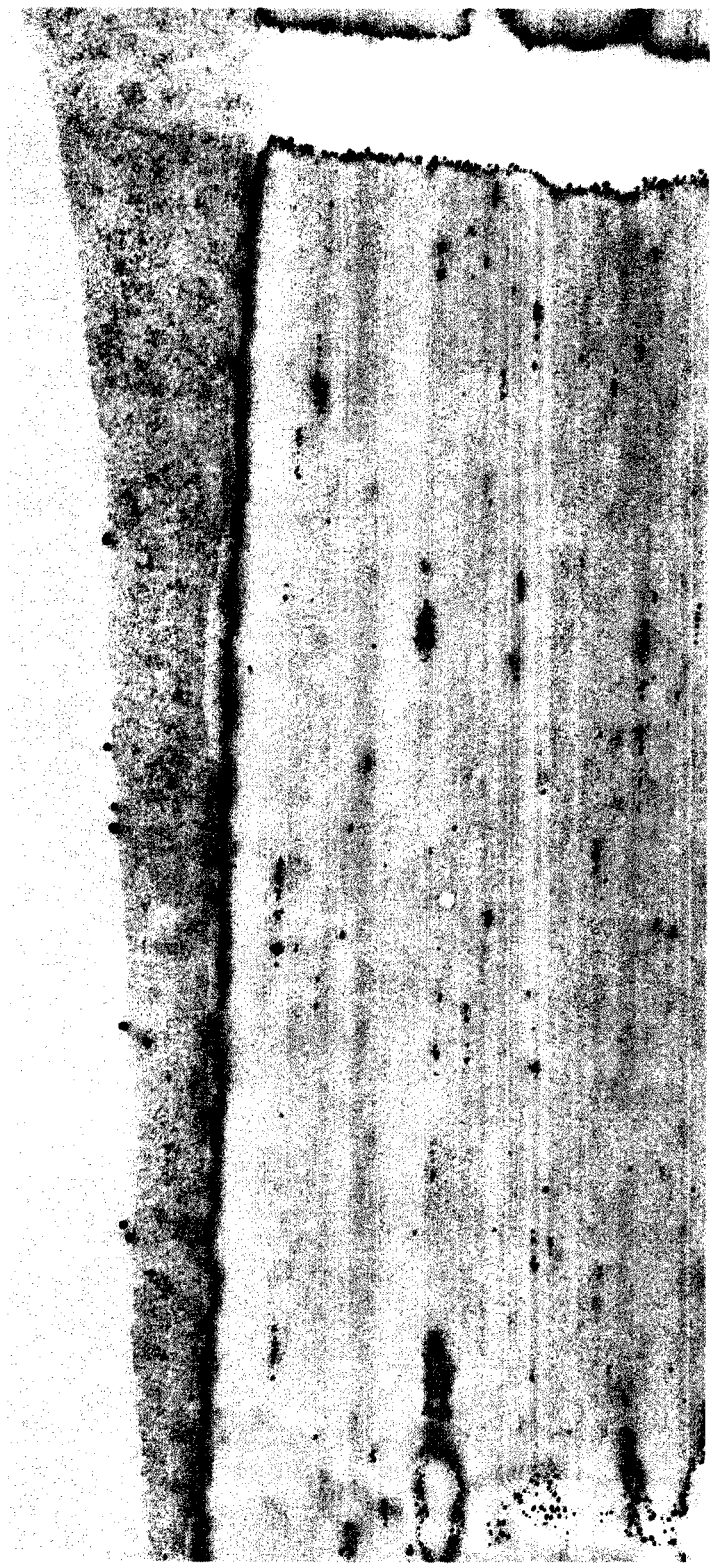
FIG. 9 shows a TEM of galactosamine-NPs in which it can be seen that many nanoparticles are bound to filters.

It was also found that galactosamine-NPs (i.e. nanoparticles having a corona of galactosamine ligands) bind strongly to filters as shown in FIG. 9.

Figure 10:
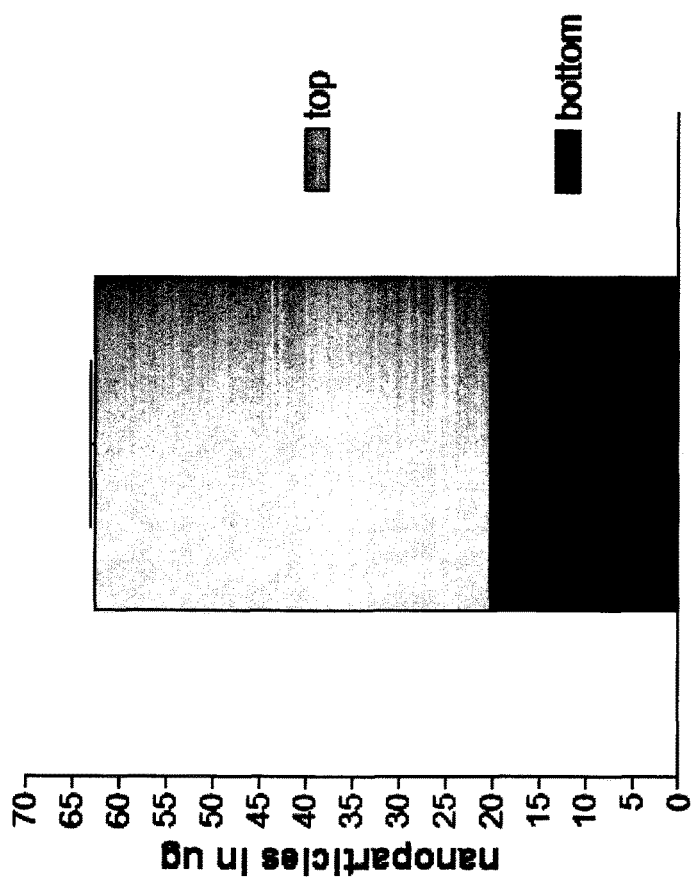
FIG. 10 shows glucose-C2 nanoparticles in µg for transendothelial transfer analysed by spectroscopy top (lightly shaded) and bottom (dark shading)

Measurement of total transendothelial transfer of C2-glucose nanoparticles is depicted in FIG. 10 (analysed by spectroscopy). The values are shown in the following table:

|  | top | bottom |  |
|---|---|---|---|
| Well 1 | 41.6 ug | 19.3 g | Applied 53.28 ug |
| Well 2 | 42.96 | 21.3 | to the top, 8 hr |
| Well 3 | 41.96 |  | incubation |

Figure 11:
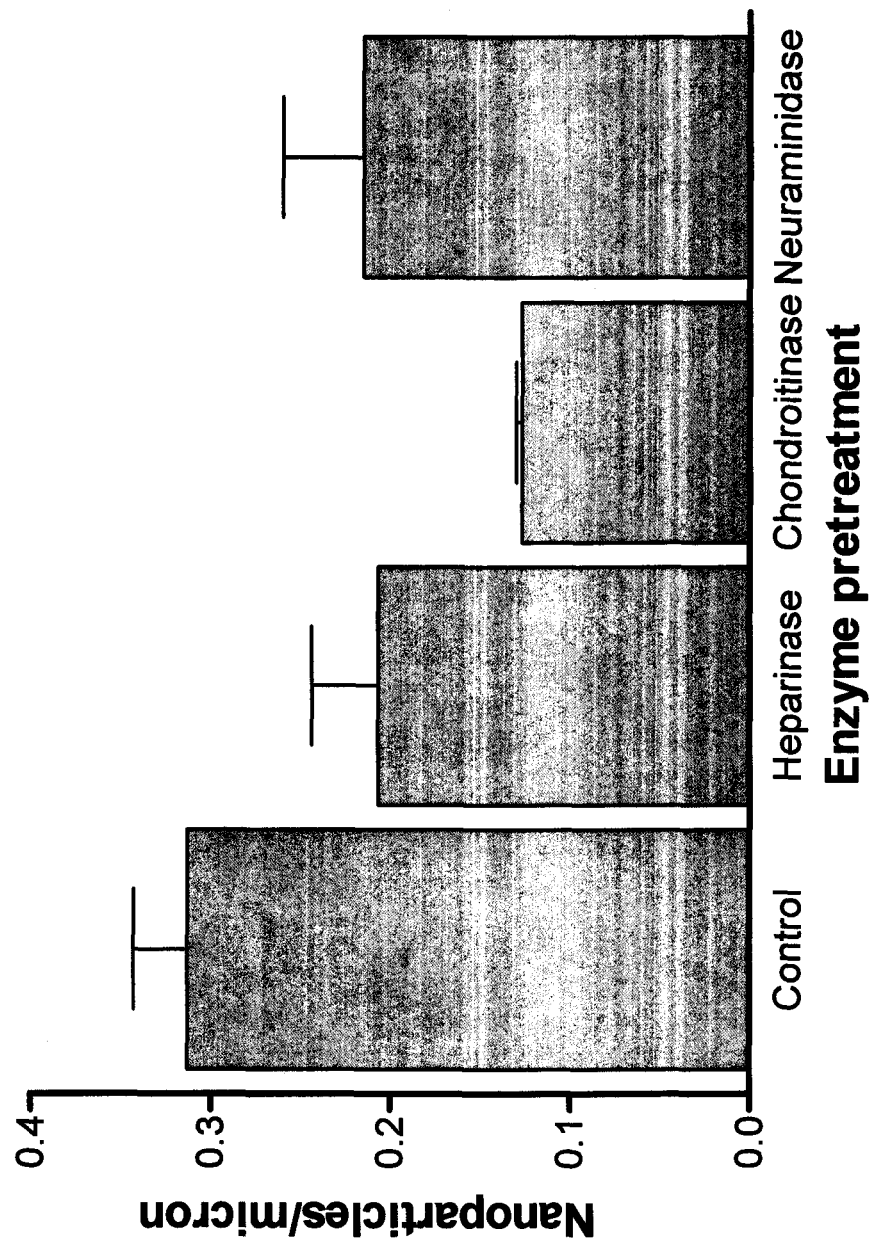
FIG. 11 shows transfer of nanoparticles measured in nanoparticles per micron for control (not enzyme pre-treated) and enzyme pre-treatment with heparinise, chondroitinase or neuraminidase measured at the basal membrane 8 hours after application of the nanoparticles.

The effect of the glycocalyx on nanoparticle transport was then investigated. Removal of glycocalyx was achieved by subjecting enthothelium cells to enzyme pre-treatment with heparinise, chondroitinase or neuraminidase and then measuring the number of nanoparticles detected per micron at the basal membrane 8 hours after application of the nanoparticles (see FIG. 11). It is evident that removal of glycocalyx inhibits transport of the nanoparticles, with the effect of chondroitinase pre-treatment being statistically significant (see ***).

Figure 12:
FIG. 12 shows a TEM depicting insulin-coated nanoparticles (8 insulins and Zinc) taken up by hCMEC/D3 cells. 2 ng/cm2 of nanoparticles were applied for 3 hours.
Figure 13:
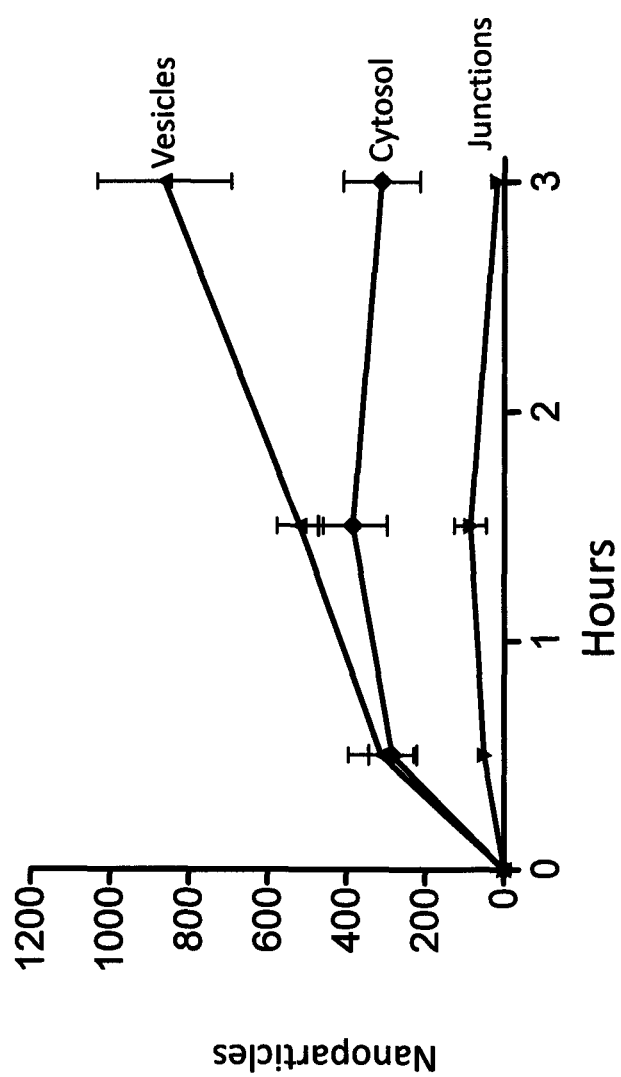
FIG. 13 shows insulin-coated nanoparticles transfer across hCMEC/D3 cells plotted against time for vesicles, cytosol and junctions.
Figure 14:
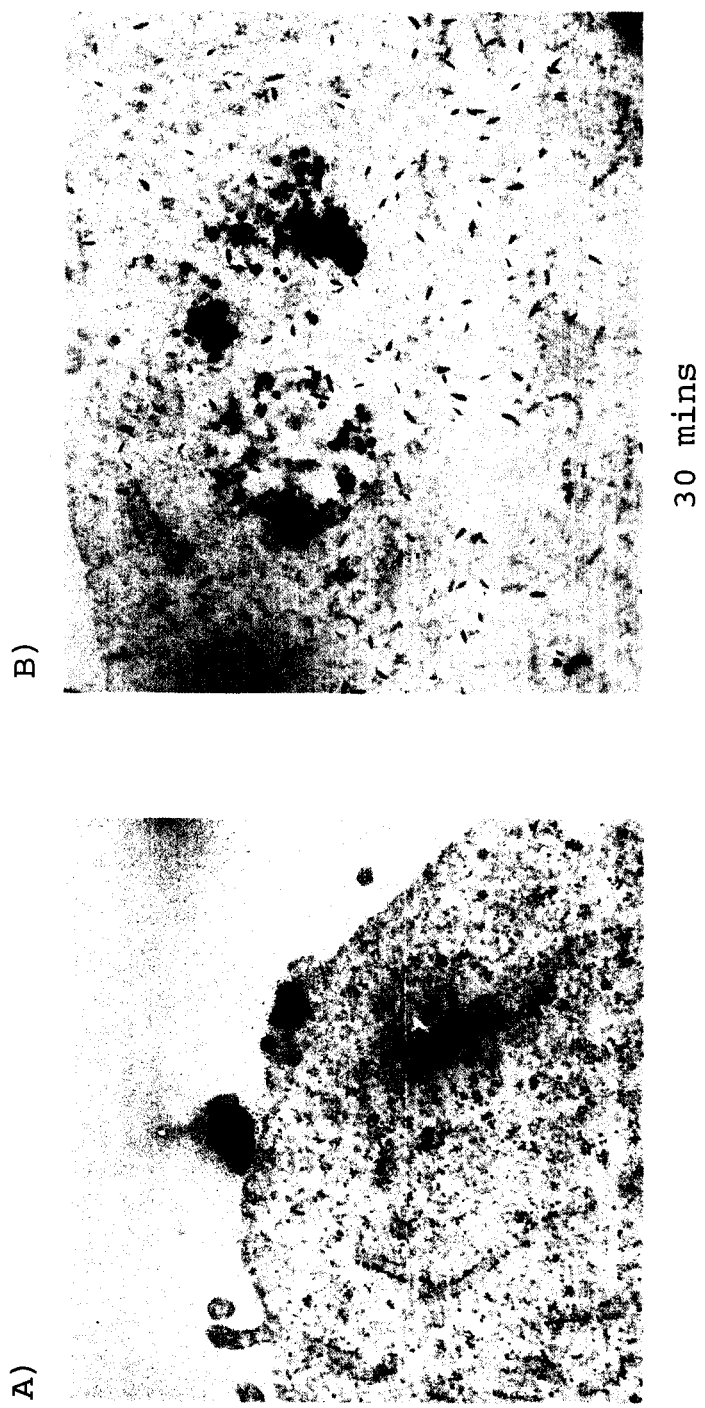
FIG. 14 shows TEM of insulin-coated nanoparticles at A) time zero and B) 30 mins with dark staining indicating nanoparticles.

FIG. 12 shows insulin-coated nanoparticles (8 insulins and Zinc) taken up by hCMEC/D3 cells. 2 ng/cm$^2$ of nanoparticles were applied for 3 hours. It was found that insulin-coated nanoparticles transfer rapidly across hCMEC/D3 cells, primarily by vesicles (see FIGS. 13 and 14A and 14B).

Figure 15:
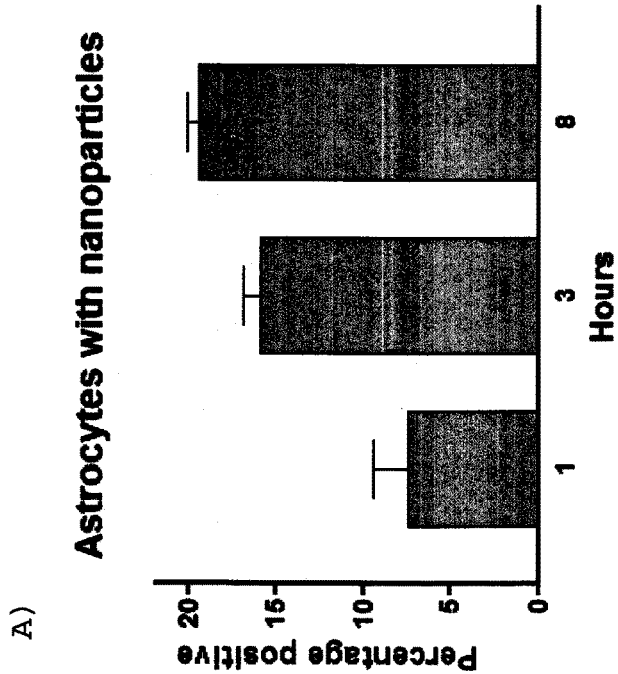
FIG. 15 shows A) the percentage of astrocytes positive with nanoparticles at 1, 3 and 8 hours; and B) the average distance of nanoparticles from the endothelium in microns (maximum distance shown in inset figure) at 1, 3 and 8 hours.

The localisation of C2-glucose nanoparticles in astrocytes was investigated. FIG. 15A shows the percentage of astrocytes positive with nanoparticles at 1, 3 and 8 hours. FIG. 15B shows the average distance of nanoparticles from the endothelium in microns (maximum distance shown in inset figure) at 1, 3 and 8 hours.

Figure 16A:
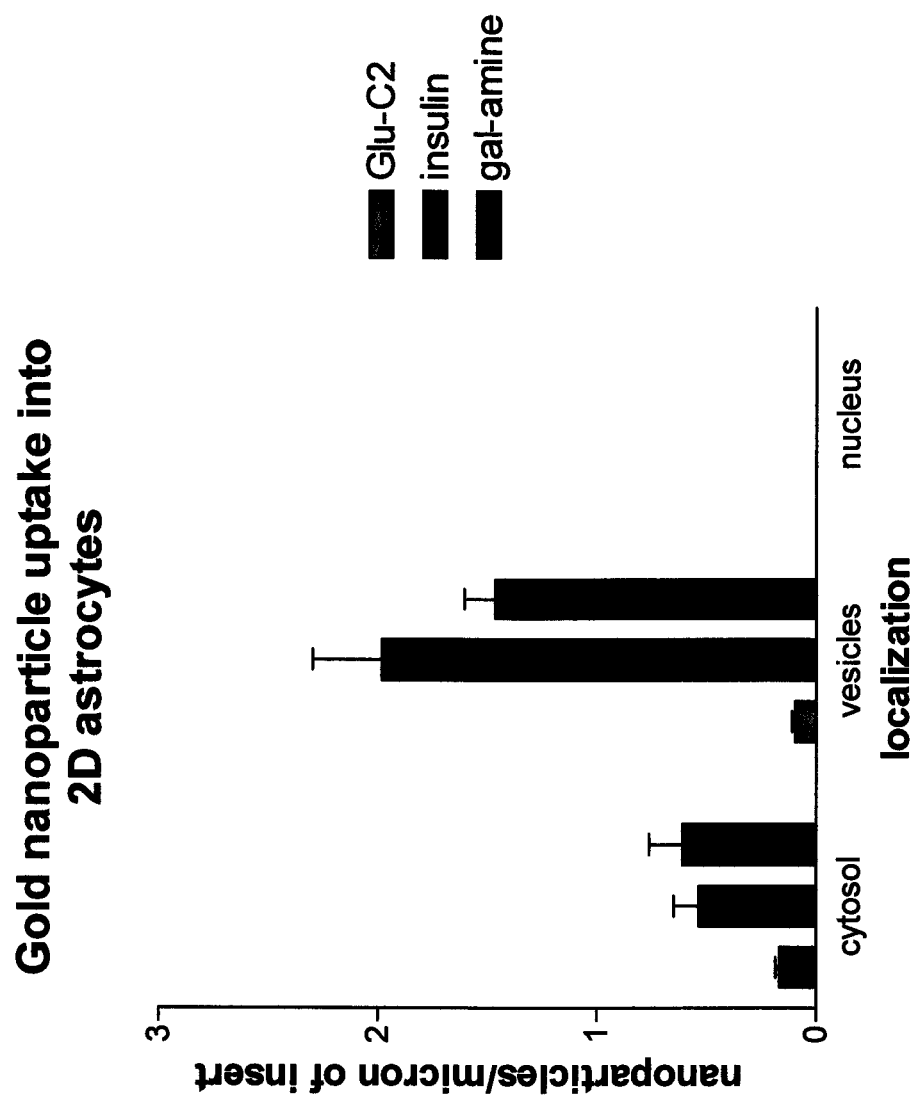
FIG. 16 shows gold nanoparticle uptake for various nanoparticle corona compositions (C2-glucose, insulin or galactosamine coatings) in A) 2D astrocyte culture and B) 3D co-cultured astrocytes. The uptake into cytosol, vesicles and nucleus are shown, measured in nanoparticles micron of insert and per cell, respectively.
Figure 16B:
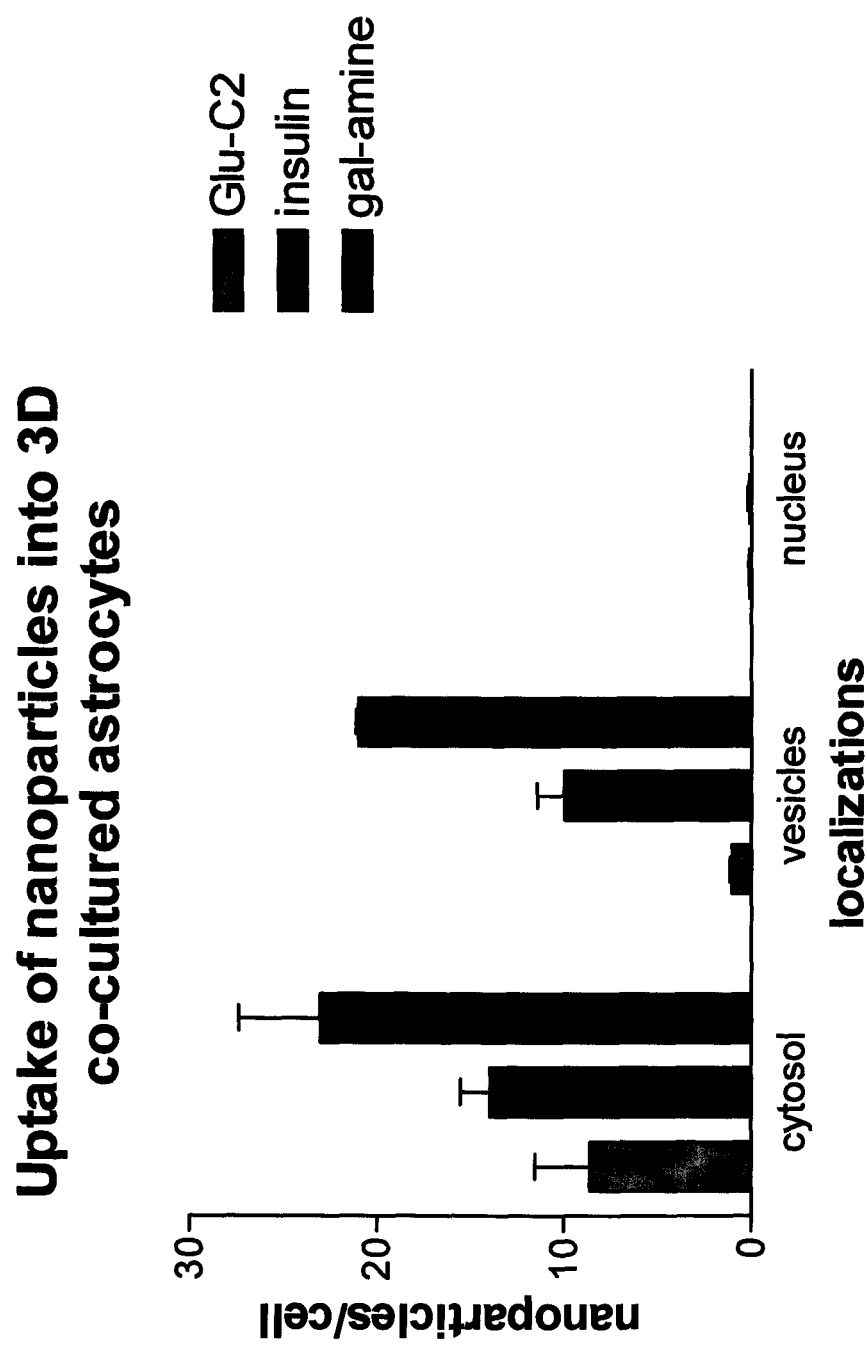

Gold nanoparticle uptake for various nanoparticle corona compositions (C2-glucose, insulin or galactosamine coatings) was investigated in 2D astrocyte culture and 3D co-cultured astrocytes (see FIGS. 16A and 16B, respectively). The uptake into cytosol, vesicles and nucleus are shown, measured in nanoparticles per cell.

Figure 17:
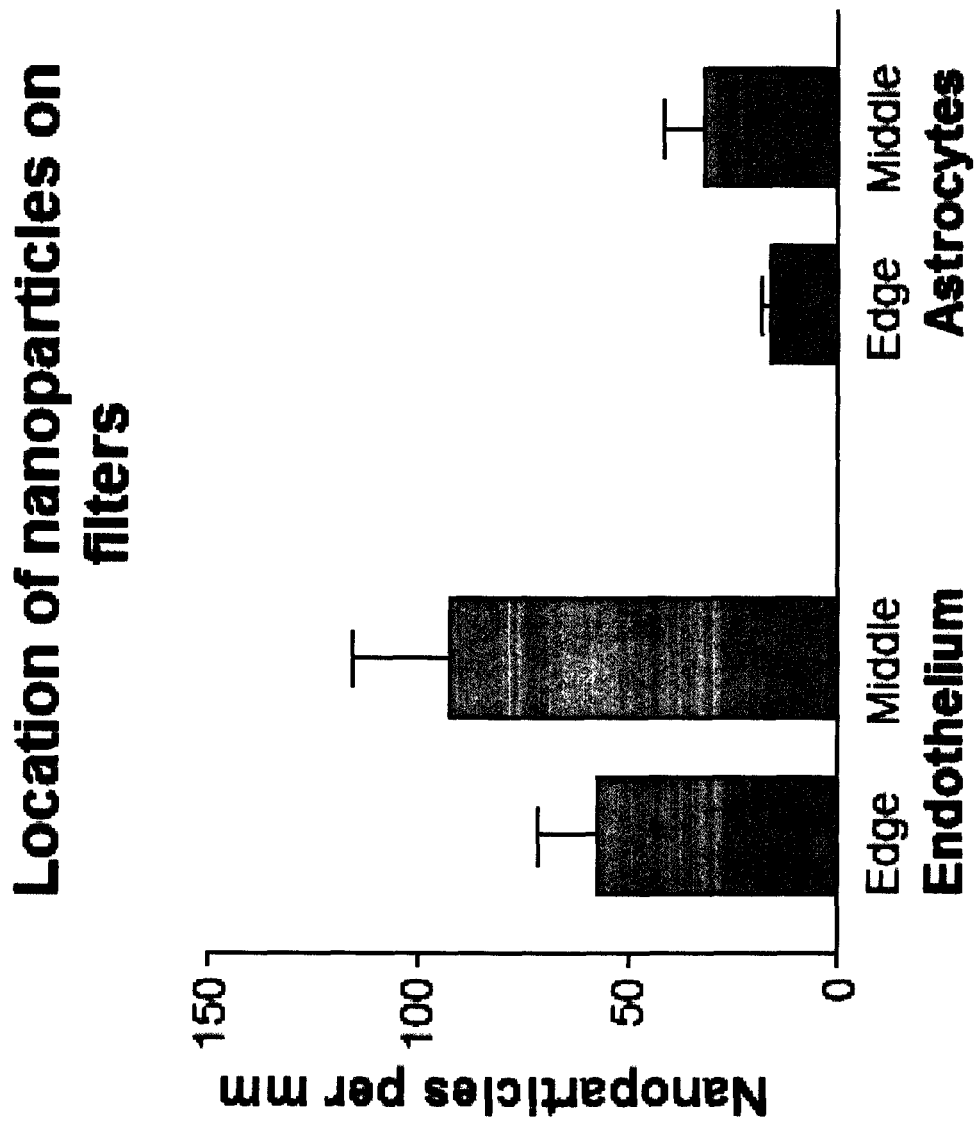
FIG. 17 shows the location of nanoparticles on filters (edge or middle) for endothelium and astrocytes. The number of nanoparticles in both endothelium and astrocytes is shown for edge and middle.

FIG. 17 shows the location of nanoparticles on filters (edge or middle) for endothelium and astrocytes. The number of nanoparticles in both endothelium and astrocytes was higher in the middle of the filters than at the edges, but this difference was not found to be statistically significant ($p > 0.05$).

Figure 18:
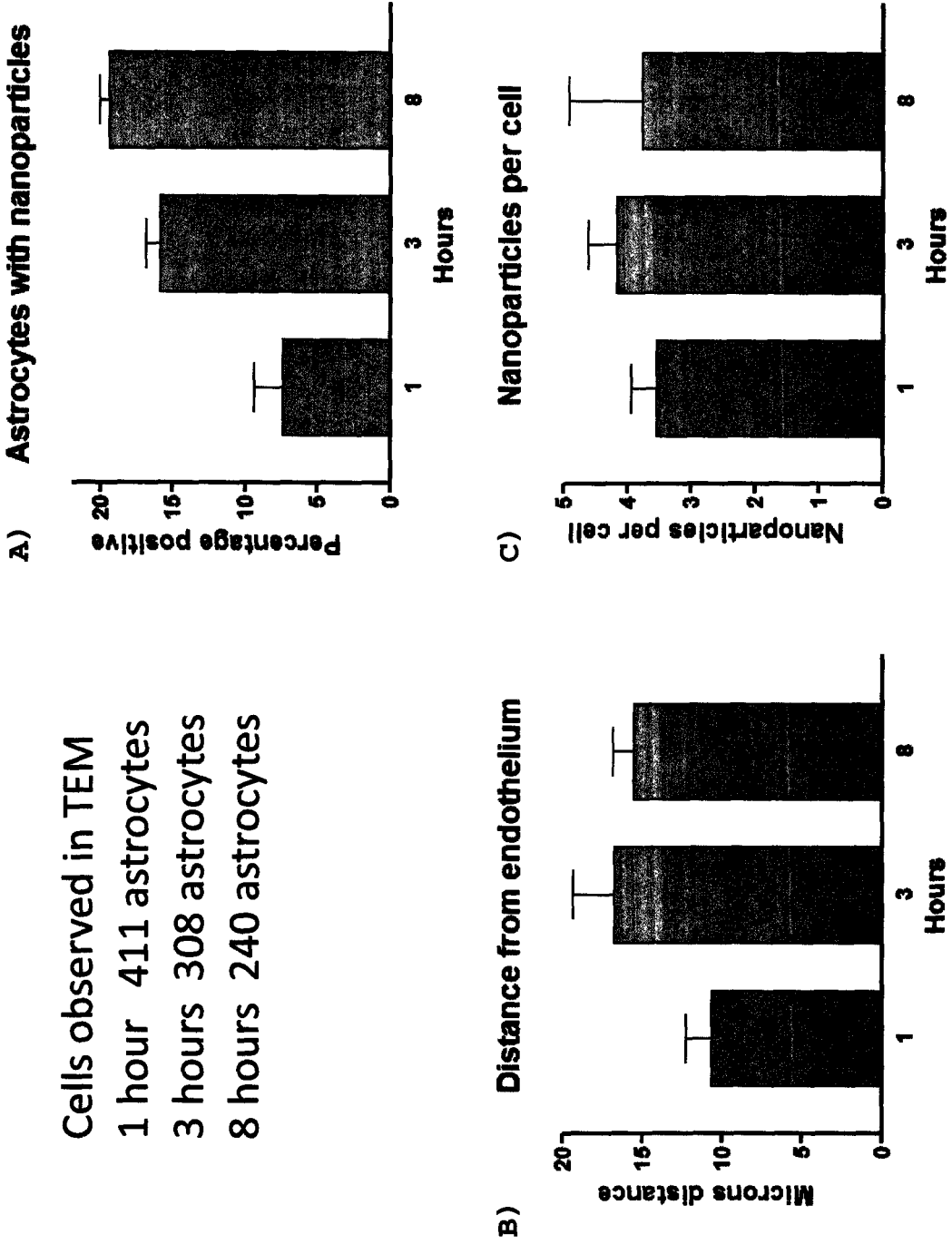
FIG. 18 shows results investigating nanoparticles in astrocyte/D3 co-culture. A) Percentage of astrocytes positive for nanoparticles at 1, 3 and 8 hours. B) distance nanoparticles found from endothelium in microns at 1, 3 and 8 hours. C) number of nanoparticles per cell at 1, 3 and 8 hours. The number of cells observed in transmission electron microscopy (TEM) at 1, 3 and 8 hours is shown in the inset.

FIG. 18 shows results investigating nanoparticles in astrocyte/D3 co-culture. A) Percentage of astrocytes positive for nanoparticles at 1, 3 and 8 hours. B) distance nanoparticles found from endothelium in microns at 1, 3 and 8 hours. C) number of nanoparticles per cell at 1, 3 and 8 hours. The number of cells observed in transmission electron microscopy (TEM) at 1, 3 and 8 hours is shown in the inset to FIG. 18.

Figure 19:
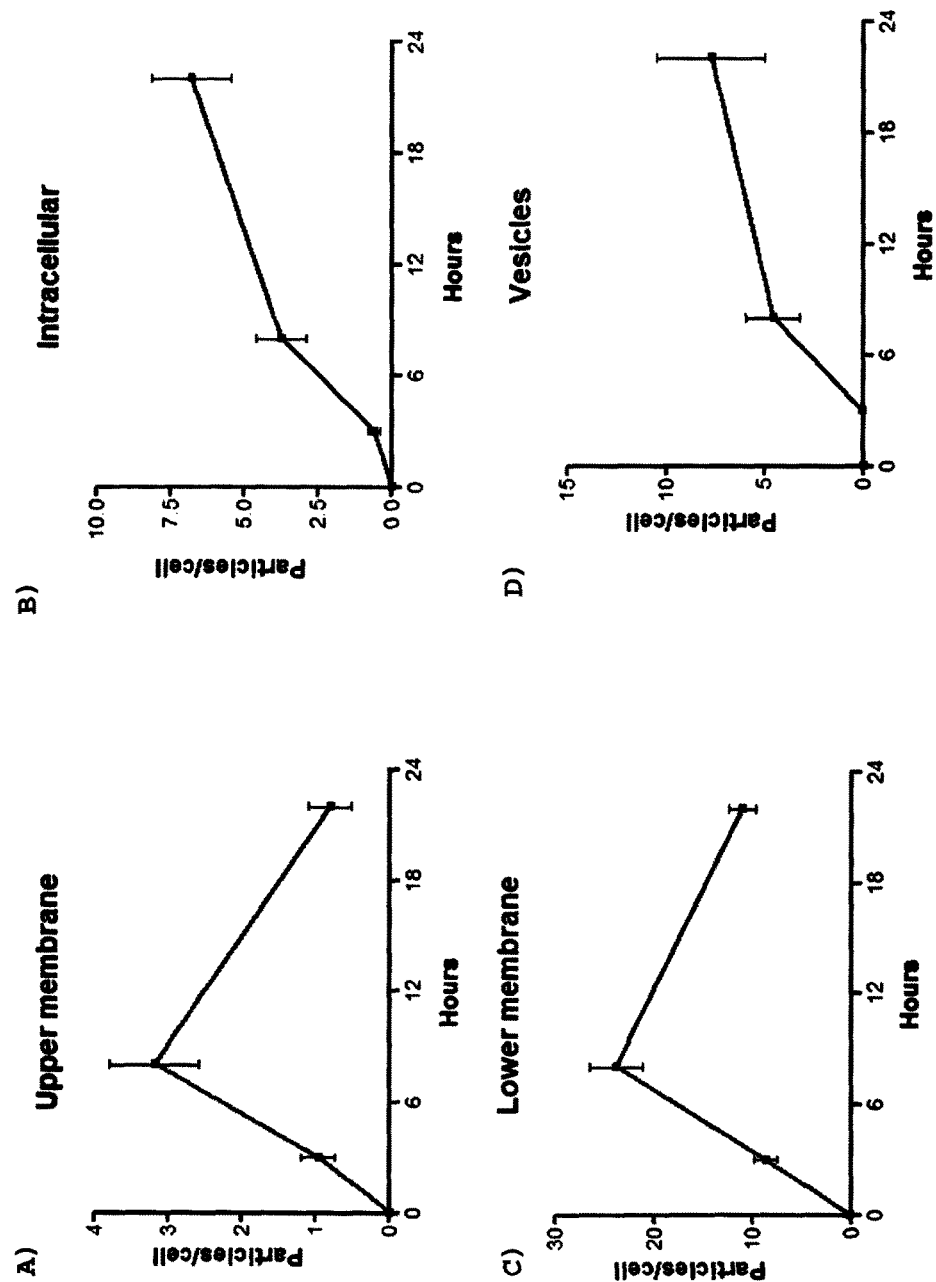
FIG. 19 shows results investigating the time course of uptake of glucose-NPs. A) Particles per cell in the upper membrane over time. B) Particles per cell in the intracellular region over time. C) Particles per cell in the lower membrane over time. D) Particles per cell in the vesicles over time.

FIG. 19 shows results investigating the time course of uptake of glucose-NPs. A) Particles per cell in the upper membrane over time. B) Particles per cell in the intracellular region over time. C) Particles per cell in the lower membrane over time. D) Particles per cell in the vesicles over time.

Figure 20:
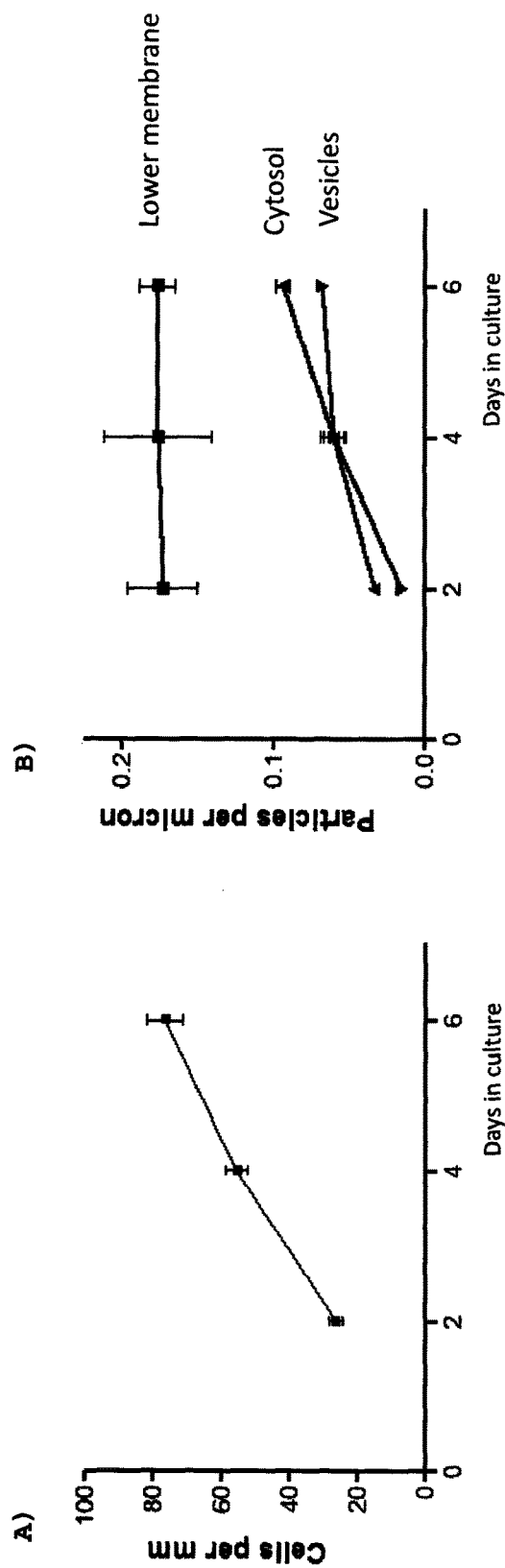
FIG. 20 shows A) number of cells per mm plotted against days in culture; and 8) the number of nanoparticles per micron at lower membrane, cytosol and vesicles plotted against days in culture.

An investigation into the possible effect of endothelial density on nanoparticle transfer was carried out. As shown in FIGS. 20A and 20B, endothelial density does not affect the nanoparticle transfer.

CONCLUSIONS

Glucose-coated nanoparticles were found to be selective for brain endothelium. Up to 70,000 nanoparticles cross each endothelial cell in an 8 hour period. Nanoparticles move at 10-20 μm per hour, with more than 400 nanoparticles reaching each astrocyte.

Galactosamine and glutathione nanoparticles also cross efficiently. Movement of glucose-coated-NPs is primarily across the cytosol. Removal of glycocalyx or reduction in temperature reduces cytosolic transfer.

Insulin-coated NPs appear to use rapid vesicular transcytosis across the endothelium. They can also be taken up by astrocytes. Without wishing to be bound by any particular theory, the present inventors contemplate that the ability to delivery insulin to the CNS via nanoparticles, as described herein, will have significant medical potential because the avoidance of unwanted hypoglycemia (e.g. due to peripheral effects of insulin) may be diminished or prevented.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

REFERENCES

1. Wolburg H, Lippoldt A, (2001) Tight junctions of the blood-brain barrier: development, composition and regulation. Vasc. Pharm. 38: 323-337.
2. Sarkadi B, Homolya L, Szakács G, Váradi A (2006) Human multi-drug resistance ABCB and ABCG transporters: Participation in a chemoimmunity defence system. Physiol Rev 86: 1179-1236.
3. Manfredsson F P and Mandel R J (2010) Development of gene therapy for neurological disorders. Discovery Medicine 9: 204-211.
4. Baker D and Hankey D J (2003) Gene therapy in autoimmune demyelinating diseases of the central nervous system. Gene therapy 10: 844-853.
5. Sloane E et al. (2009) Anti-inflammatory cytokine gene therapy decreases sensory and motor dysfunction in experimental Multiple Sclerosis. Brain Behav Immun. 23: 92-100.
6. Deverman B E and Patterson P H (2012) Exogenous Leukemia Inhibitory Factor Stimulates Oligodendrocyte Progenitor Cell Proliferation and Enhances Hippocampal Remyelination. J. Neurosci 32: 2100-2109.
7. Patel T et al (2012) Polymeric nanoparticles for drug delivery to the central nervous system. Advanced. Drug Delivery Revs 64: 701-705.
8. Kanwar et al. (2012) Nanoparticles in the treatment and diagnosis of neurological disorders: untamed dragon with the fire power to heal. Nanomedicine: nanotechnology, Biology and Medicine 8: 399-414.
9. Sonavane G, Tomoda K, Makino K (2008) Biodistribution of colloidal gold nanoparticles after intravenous administration: Effect of particle size. Colloids and Surfaces Biointerfaces 66: 274-280.
10. Chen Y S, Hung Y C, Liau I, Huang S (2009) Assessment of the In Vivo Toxicity of Gold Nanoparticles. Nanoscale Res Lett 4:858-864.
11. Etame, A B, Smith C A, Chan W C W, Rutka J T (2011) Design and potential application of PEGylated gold nanoparticles with size-dependent permeation through brain microvasculature. Nanomedicine: NBM 7:992-1000
12. Gao H J, Shi W D, Freund L B (2005). Mechanics of receptor-mediated endocytosis. Proc Natl Acad Sci USA 102: 9469-9474.
13. Zhang S, Li J, Lukotrafitis G, Bao G, Suresh S (2009) Size-dependent endocytosis of nanoparticles. Adv. Mater. 21: 419-424.
14. Shan Y, Ma S, Nie L, Shang X, Hao X, Tang Z, Wang H (2011). Size-dependent endocytosis of single gold nanoparticles. Chem Commun 47: 8091-8093.
15. Alkilany A M, Murphy C J (2010) Toxicity and cellular uptake of gold nanoparticles: what we have learned so far? J Nanopart Res 12: 2313-2333
16. Zensi A, Begley D, Pontikis C, Legros C, Mihoreanu L, Rachel C, Kreuter J (2010) Human serum albumin nanoparticles modified with apolipoprotein A-I cross the blood-brain barrier and enter the rodent brain. *Journal of Drug Targeting* 10: 842-848.
17. Chen L, Yokel R A, Hennig B, Toborek M (2008) Manufactured aluminium oxide nanoparticles decrease expression of tight junction proteins in brain vasculature. J Neuroimmune Pharmacol 3: 286-295.
18. Georgieva J V et al. (2011) Surface characteristics of nanoparticles determine their intracellular fate in processing by human blood-brain barrier endothelial cells in vitro. Molecular Therapy 19: 318-325.
19. Chithrani B D, Ghazani A A, Chan W C (2006) Determining the size and shape dependence of gold nanoparticles uptake by mammalian cells. Nano Lett 6: 662-668.
20. Wang Y Y et al (2009) Receptor mediated therapeutic transport across the blood brain barrier. Immunotherapy, Vol. 1, No. 6: 983-993.
21. Morgello S et al (1995) The human blood brain barrier transporter (GLUT1) is a glucose transporter of gray matter astrocytes. Glia 14: 43-54.
22. Lund T, Callaghan M F, Williams P, Turmaine M, Bachmann C, Rademacher T, Roitt I M, Bayford R (2011) The influence of ligand organization on the rate of uptake of gold nanoparticles by colorectal cancer cells. Biomaterials 32: 9776-9784.
23. East E, Golding J P Phillips J B (2009) A versatile 3D culture model facilitates monitoring of astrocytes undergoing reactive gliosis. J Tissue Eng. Regen. Med. 8: 634-646.
24. East E, Golding J P, Phillips J B (2012) Engineering an integrated cellular interface in three-Dimensional hydrogel cultures permits monitoring of reciprocal astrocyte and neuronal responses. Tissue Eng Part C Methods. Epub ahead of print PMID:22235832.
25. Weksler B B, Subileau E A, Perriere N, Charneau P, Holloway K, Leveque M, Tricoire-Leignel H, Nicotra A, Bourdoulous S, Turowski P, Male D K, Roux F, Greenwood J, Romero I A, Couraud P-O (2005) Blood brain barrier specific properties of a human adult brain endothelial cell line, Faseb J. 19: 1872-1874.
26. Male D K (1995) Brain Endothelium. In "Neural Cell Culture" Edited Cohen and Wilkin, for The Practical Approach Series, IRL Press, Oxford, UK.
27. de la Fuente J M, Berry C C (2005) Tat peptide as an efficient molecule to translocate gold nanoparticles into the cell nucleus. Bioconjug Chem. 16:1176-80.
28. Male K B, Lachance B, Hrapovic S, Sunahara G, Luong J H (2008) Assessment of cytotoxicity of quantum dots and gold nanoparticles using cell-based impedance spectroscopy. Anal Chem. 80:5487-93.
29. Gannon C J, Patra C R, Bhattacharya R, Mukherjee P, Curley S A (2008) Intracellular gold nanoparticles enhance non-invasive radiofrequency thermal destruction of human gastrointestinal cancer cells. J. Nanobiotechnology 6:2.

30. Santos W L C, Rahman J, Klein N and Male D K (1996) Control of lymphocyte adhesion to brain endothelium: ICAM-1, VCAM-1 and negative charge. J. Neuroimmunol, 66, 125-134
31. Gu Y J, Cheng J, Lin C C, Lam Y W, Cheng S H, Wong W T (2009) Nuclear penetration of surface functionalized gold nanoparticles. Toxicol Appl Pharmacol. 237:196-204.
32. Cho E C, Zhang Q, Xia Y (2011) The effect of sedimentation and diffusion on cellular uptake of gold nanoparticles. Nat. Nanotechnol. 6:385-91.
33. Gromnicova R, et al. (2013) Glucose-Coated Gold Nanoparticles Transfer across Human Brain Endothelium and Enter Astrocytes In Vitro. PLoS ONE 8(12): e81043, pp. 1-10.

The invention claimed is:

1. A method of treating a central nervous system (CNS) disorder in a mammalian subject, said CNS disorder being selected from the group consisting of: a tumour of the CNS; a neurodegenerative disease; stroke; a neurological disorder; an infection of the CNS; an immune disorder of the CNS; a psychiatric disorder; a genetic abnormality affecting the CNS; and a traumatic brain injury, said method comprising administering a therapeutically effective amount of a composition to the subject suffering from said CNS disorder, said composition comprising:
   (a) a nanoparticle comprising:
      (i) a core consisting of a metal selected from the group consisting of: Au, Ag, Cu, Pt, Pd and any combination thereof, wherein the diameter of the core is in the range 1 nm to 5 nm;
      (ii) a corona comprising a plurality of ligands each covalently linked to the core via a sulphur-containing group, wherein said ligands comprise glutathione and/or a monosaccharide or disaccharide carbohydrate selected from the group consisting of: glucose, alpha galactose, mannose, fucose, maltose, and lactose, wherein the monosaccharide or disaccharide carbohydrate is linked to the sulphur-containing group via a C2-C15 alkyl and/or C2-C15 glycol linker, and wherein the diameter of the nanoparticle including said ligands is in the range 3 nm to 10 nm; and
   (b) at least two entities of an agent covalently attached to said core directly or via a linker, each of which at least two entities of agent exhibit at least one therapeutic effect against said CNS disorder.

2. A method of treating a central nervous system (CNS) disorder in a mammalian subject, said CNS disorder being selected from the group consisting of: a tumour of the CNS; a neurodegenerative disease; stroke; a neurological disorder; an infection of the CNS; an immune disorder of the CNS; a psychiatric disorder; a genetic abnormality affecting the CNS; and a traumatic brain injury, said method comprising administering a therapeutically effective amount of a composition to the subject suffering from said CNS disorder, said composition comprising:
   (a) a nanoparticle comprising:
      (i) a core consisting of a metal selected from the group consisting of: Au, Ag, Cu, Pt, Pd and any combination thereof, wherein the diameter of the core is in the range 1 nm to 5 nm;
      (ii) a corona comprising a plurality of ligands each covalently linked to the core via a sulphur-containing group, wherein said ligands comprise glutathione and/or a monosaccharide or disaccharide carbohydrate selected from the group consisting of: glucose, alpha galactose, mannose, fucose, maltose, and lactose, wherein the monosaccharide or disaccharide carbohydrate is linked to the sulphur-containing group via a C2-C15 alkyl and/or C2-C15 glycol linker, and wherein the diameter of the nanoparticle including said ligands is in the range 3 nm to 10 nm; and
   (b) at least two different species of agent covalently attached to said core directly or via a linker, each of which at least two species of agent exhibits at least one therapeutic effect against said CNS disorder.

3. A method of treating a central nervous system (CNS) disorder in a mammalian subject, said CNS disorder being selected from the group consisting of: a tumour of the CNS; a neurodegenerative disease; stroke; a neurological disorder; an infection of the CNS; an immune disorder of the CNS; a psychiatric disorder; a genetic abnormality affecting the CNS; and a traumatic brain injury, said method comprising administering a therapeutically effective amount of a composition to the subject suffering from said CNS disorder, said composition comprising:
   (a) a nanoparticle comprising:
      (i) a core consisting of a metal selected from the group consisting of: Au, Ag, Cu, Pt, Pd and any combination thereof, wherein the diameter of the core is in the range 1 nm to 5 nm;
      (ii) a corona comprising a plurality of ligands each covalently linked to the core via a sulphur-containing group, wherein said ligands comprise glutathione and/or a monosaccharide or disaccharide carbohydrate selected from the group consisting of: glucose, alpha galactose, mannose, fucose, maltose, and lactose, wherein the monosaccharide or disaccharide carbohydrate is linked to the sulphur-containing group via a C2-C15 alkyl and/or C2-C15 glycol linker, and wherein the diameter of the nanoparticle including said ligands is in the range 3 nm to 10 nm; and
   (b) at least one agent covalently attached to said core directly or via a linker, which agent exhibits at least one therapeutic effect against said CNS disorder, the at least one agent being selected from the group consisting of: loprazolam, lormetazepam, temazepam; zaleplon, zolpidem, zopiclone; clomethiazole; promethazine; melatonin; buspirone; chlorpromazine hydrochloride, haloperidol, perphenazine, prochlorperazine maleate or mesilate, promazine hydrochloride, trifluoperazine; clozapine, Olanzapine, quetiapine, carbamazepine and sodium valproate; amitriptyline hydrochloride, clomipramine hydrochloride, imipramine hydrochloride; mianserin hydrochloride; phenelzine, moclobemide; citalopram, fluoxetine, sertraline; agomelatine, flupentixol, tryptophan, venlafaxine; atomoxetine, methylphenidate hydrochloride, modafinil; cyclizine hydrochloride, chlorpromazine, droperidol, prochlorperazine maleate, metoclopramide hydrochloride, ondansetron, palonosetron, fosaprepitant, nabilone, betahistine dihydrochloride; nefopam hydrochloride; buprenorphine; diamorphine hydrochloride, fentanyl, meptazinol, tramadol hydrochloride; capsaicin; tolfenamic acid, zolmitriptan, pizotifen, clonidine; everolimus, temozolomide, carmustine; Glatiramer acetate and fingolimod.

* * * * *